(12) United States Patent
Anklin-Imhof et al.

(10) Patent No.: US 8,333,119 B2
(45) Date of Patent: *Dec. 18, 2012

(54) MEASURING TRANSDUCER OF VIBRATION-TYPE, AS WELL AS AN IN-LINE MEASURING DEVICE HAVING SUCH A MEASURING TRANSDUCER

(75) Inventors: Martin Anklin-Imhof, Dornach (CH); Ennio Bitto, Aesch (CH); Christof Huber, Bern (CH); Alfred Rieder, Landshut (DE)

(73) Assignee: Endress + Hauser Flowtec AG, Reinach (CH)

( * ) Notice: Subject to any disclaimer, the term of this patent is extended or adjusted under 35 U.S.C. 154(b) by 0 days.

This patent is subject to a terminal disclaimer.

(21) Appl. No.: 12/659,530

(22) Filed: Mar. 11, 2010

(65) Prior Publication Data

US 2011/0259123 A1 Oct. 27, 2011

Related U.S. Application Data

(60) Provisional application No. 61/202,543, filed on Mar. 11, 2009, provisional application No. 61/213,742, filed on Jul. 9, 2009.

(30) Foreign Application Priority Data

Mar. 11, 2009 (DE) .......................... 10 2009 001 472
Jul. 9, 2009 (DE) .......................... 10 2009 027 580

(51) Int. Cl.
*G01F 1/84* (2006.01)
(52) U.S. Cl. ................................. 73/861.357

(58) Field of Classification Search .................. None
See application file for complete search history.

(56) References Cited

U.S. PATENT DOCUMENTS

| 5,230,254 | A | 7/1993 | Craft | |
|---|---|---|---|---|
| 7,127,952 | B2 * | 10/2006 | Bitto et al. | 73/861.355 |
| 7,350,422 | B2 * | 4/2008 | Bitto et al. | 73/861.355 |
| 7,946,187 | B2 | 5/2011 | Hussain | |
| 2010/0236338 | A1 * | 9/2010 | Bitto et al. | 73/861.357 |
| 2010/0242623 | A1 * | 9/2010 | Bitto et al. | 73/861.356 |
| 2010/0242624 | A1 * | 9/2010 | Bitto et al. | 73/861.357 |

(Continued)

FOREIGN PATENT DOCUMENTS

EP 0 119 638 9/1984

(Continued)

OTHER PUBLICATIONS

English translation of the International Preliminary Examination Report.

*Primary Examiner* — Harshad R Patel
(74) *Attorney, Agent, or Firm* — Bacon & Thomas, PLLC

(57) ABSTRACT

A measuring transducer includes: a transducer housing with an inlet-side flow divider having exactly four flow openings and an outlet-side flow divider having exactly four flow openings; as well as exactly four, straight, measuring tubes connected to the flow dividers. Each of the four measuring tubes opens into one the flow openings of the inlet-side flow divider and into one the flow openings of the outlet-side flow divide. Additionally, the measuring transducer includes an electromechanical exciter mechanism for producing and/or maintaining mechanical oscillations of the measuring tubes such that the measuring tubes are excitable pairwise to execute opposite phase bending oscillations in a shared imaginary plane of oscillation.

54 Claims, 11 Drawing Sheets

U.S. PATENT DOCUMENTS

| | | | | |
|---|---|---|---|---|
| 2010/0251830 | A1* | 10/2010 | Bitto et al. | 73/861.357 |
| 2011/0146383 | A1* | 6/2011 | Bitto et al. | 73/30.03 |
| 2011/0146416 | A1* | 6/2011 | Bitto et al. | 73/861.357 |
| 2011/0167907 | A1* | 7/2011 | Bitto et al. | 73/32 A |
| 2011/0265580 | A1* | 11/2011 | Huber et al. | 73/861.357 |

FOREIGN PATENT DOCUMENTS

| | | |
|---|---|---|
| EP | 2 159 552 | 3/2010 |
| WO | WO 96/08697 | 3/1996 |
| WO | WO 02/052230 A1 | 7/2002 |

\* cited by examiner

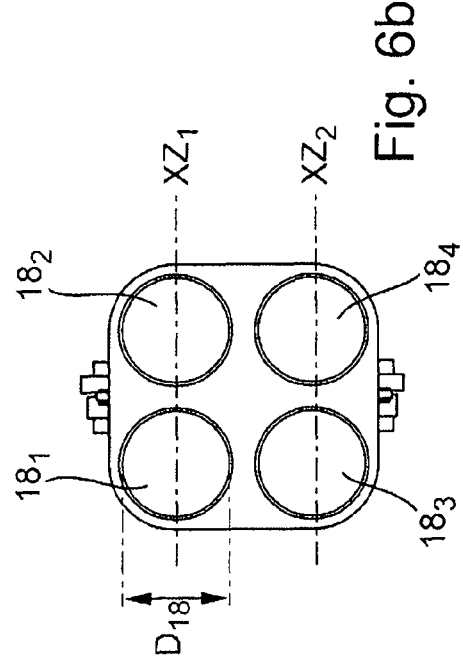
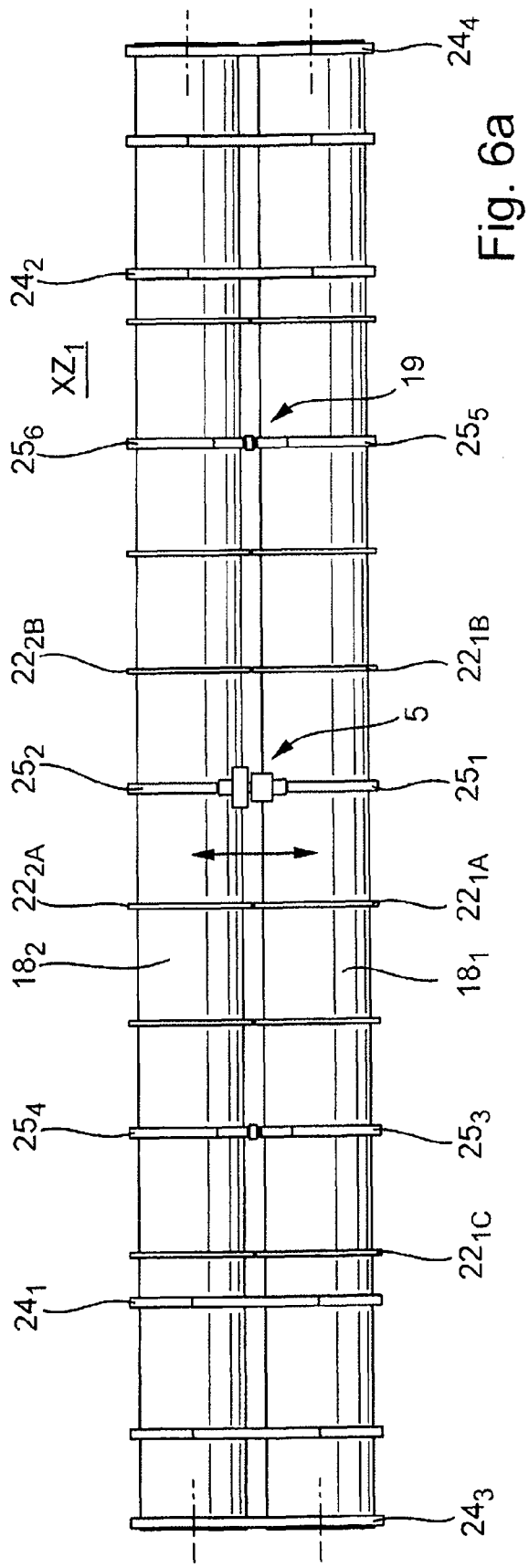

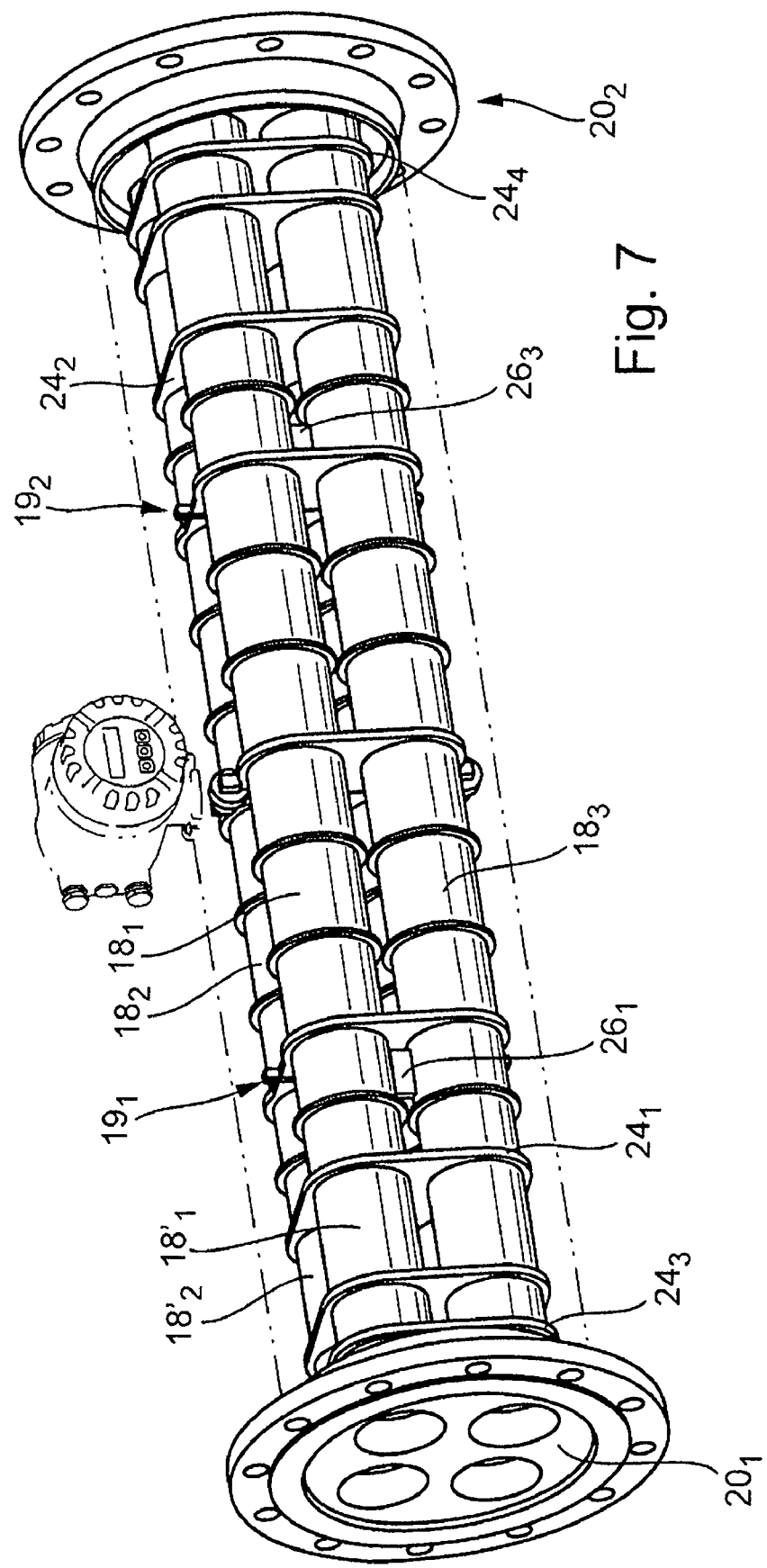

US 8,333,119 B2

MEASURING TRANSDUCER OF VIBRATION-TYPE, AS WELL AS AN IN-LINE MEASURING DEVICE HAVING SUCH A MEASURING TRANSDUCER

CROSS-REFERENCE TO RELATED APPLICATION

This application is a Nonprovisional application, which claims the benefit of U.S. Provisional Application No. 61/202,543, filed on Mar. 11, 2009, and also U.S. Provisional Application 61/213,742, filed on Jul. 9, 2009. This application is a National stage application of PCT/EP10/053126 filed Mar. 11, 2010.

TECHNICAL FIELD

The invention relates to a measuring transducer of vibration-type for measuring a medium flowably guided in a pipeline, especially a gas, liquid, powder or other flowable material, especially for measuring a density and/or a mass flow rate, especially also a mass flow integrated over a time interval, of a medium flowing in a pipeline, at least at times, with a mass flow rate of more than 2200 t/h, especially more than 2500 t/h. Additionally, the invention relates to an in-line measuring device having such a measuring transducer.

BACKGROUND DISCUSSION

Often used in process measurements, and automation, technology for measuring physical parameters, such as e.g. the mass flow, the density and/or the viscosity, of media flowing in pipelines are in-line measuring devices, which, by means of a measuring transducer of vibration-type, through which medium flows, and a measuring, and operating, circuit connected thereto, effect, in the medium, reaction forces, such as e.g. Coriolis forces corresponding with mass flow, inertial forces corresponding with density of the medium and/or frictional forces corresponding with viscosity of the medium, etc., and produce derived from these a measurement signal representing the particular mass flow, viscosity and/or density of the medium. Such measuring transducers, especially measuring transducers embodied as Coriolis, mass flow meters or Coriolis, mass flow/densimeters, are described at length and in detail e.g. in EP-A 1 001 254, EP-A 553 939, U.S. Pat. No. 4,793,191, US-A 2002/0157479, US-A 2006/0150750, US-A 2007/0151368, U.S. Pat. No. 5,370,002, U.S. Pat. No. 5,796,011, U.S. Pat. No. 6,308,580, U.S. Pat. No. 6,415,668, U.S. Pat. No. 6,711,958, U.S. Pat. No. 6,920,798, U.S. Pat. No. 7,134,347, U.S. Pat. No. 7,392,709, or WO-A 03/027616.

Each of the measuring transducers includes a transducer housing, of which an inlet-side, first housing end is formed at least partially by means of a first flow divider having exactly two, mutually spaced, circularly cylindrical, or tapered or conical, flow openings and an outlet-side, second housing end is formed at least partially by means of a second flow divider having exactly two, mutually spaced, flow openings. In the case of some of the measuring transducers illustrated in U.S. Pat. No. 5,796,011, U.S. Pat. No. 7,350,421, or US-A 2007/0151368, the transducer housing comprises a rather thick walled, circularly cylindrical, tubular segment, which forms at least a middle segment of the transducer housing.

For guiding the medium, which flows, at least at time's, the measuring transducers include, furthermore, in each case, exactly two measuring tubes of metal, especially steel or titanium, which are connected such that the medium can flow in parallel and which are positioned within the transducer housing and held oscillatably therein by means of the aforementioned flow dividers. A first of the, most often, equally constructed and, relative to one another, parallel extending, measuring tubes opens with an inlet-side, first, measuring tube end into a first flow opening of the inlet-side, first flow divider and with an outlet-side, second measuring tube end into a first flow opening of the outlet-side, second flow divider and a second of the measuring tubes opens with an inlet-side, first measuring tube end into a second flow opening of the first flow divider and with an outlet-side, second measuring tube end into a second flow opening of the second flow divider. Each of the flow dividers includes additionally, in each case, a flange with a sealing surface for fluid tight connecting of the measuring transducer to tubular segments of the pipeline serving, respectively, for supplying and removing medium to and from the measuring transducer.

For producing the above discussed reaction forces, the measuring tubes are caused to vibrate during operation, driven by an exciter mechanism serving for producing, or maintaining, as the case may be, mechanical oscillations, especially bending oscillations, of the measuring tubes in the so-called wanted mode. The oscillations in the wanted mode are, most often, especially in the case of application of the measuring transducer as a Coriolis, mass flow meter and/or densimeter, developed, at least partially, as lateral bending oscillations and, in the case of medium flowing through the measuring tubes, as a result of therein induced Coriolis forces, as additional, equal frequency oscillations superimposed in the so-called Coriolis mode. Accordingly, the—here most often electrodynamic—exciter mechanism is, in the case of straight measuring tubes, embodied in such a manner, that, therewith, the two measuring tubes are excitable in the wanted mode, at least partially, especially also predominantly, to opposite phase bending oscillations in a shared plane of oscillation, differentially—thus through introduction of exciter forces acting simultaneously along a shared line of action, however, in opposed direction.

For registering vibrations, especially bending oscillations, of the measuring tubes excited by means of the exciter mechanism and for producing oscillation measurement signals representing vibrations, the measuring transducers have, additionally, in each case, a, most often, likewise electrodynamic, sensor arrangement reacting to relative movements of the measuring tubes. Typically, the sensor arrangement is formed by means of an inlet-side, oscillation sensor registering oscillations of the measuring tubes differentially—thus only relative movements of the measuring tubes—as well as by means of an outlet-side, oscillation sensor registering oscillations of the measuring tubes differentially. Each of the oscillation sensors, which are usually constructed equally with one another, is formed by means of a permanent magnet held on the first measuring tube and a cylindrical coil held on the second measuring tube and permeated by the magnetic field of the permanent magnet.

In operation, the above described inner part of the measuring transducer, formed by means of the two measuring tubes as well as the thereon held exciter mechanism and sensor arrangement, is excited by means of the electromechanical exciter mechanism, at least at times, to execute mechanical oscillations in the wanted mode at at least one dominating, wanted, oscillation frequency. Selected as oscillation frequency for the oscillations in the wanted mode is, in such case, usually a natural, instantaneous, resonance frequency of the inner part, which, in turn, depends essentially both on size, shape and material of the measuring tubes as well as also on an instantaneous density of the medium; in given cases, this wanted oscillation frequency can also be influenced significantly by an instantaneous viscosity of the medium. As a result of fluctuating density of the medium being measured and/or as a result of media change occurring during operation, the wanted oscillation frequency during operation of the measuring transducer varies naturally, at least within a calibrated and, thus, predetermined, wanted frequency band, which correspondingly has a predetermined lower, and a predetermined upper, limit frequency.

For defining a free, oscillatory length of the measuring tubes and, associated therewith, for adjusting the band of the wanted frequency, measuring transducers of the above described type include, additionally, most often, at least one inlet-side, coupling element, which is affixed to both measuring tubes and spaced from the two flow dividers, for forming inlet-side, oscillation nodes for opposite phase vibrations, especially bending oscillations, of both measuring tubes, as well as at least one outlet-side, coupling element, which is affixed to both measuring tubes and spaced both from the two flow dividers, as well as also from the inlet-side, coupling element, for forming outlet-side, oscillation nodes for opposite phase vibrations, especially bending oscillations, of the measuring tubes. In the case of straight measuring tubes, in such case, a minimum separation between inlet side and outlet side coupling elements (which, thus, belong to the inner part) corresponds to the free, oscillatory length of the measuring tubes. By means of the coupling elements, additionally also an oscillation quality factor of the inner part, as well as also the sensitivity of the measuring transducer, in total, can be influenced, in a manner such that, for a minimum required sensitivity of the measuring transducer, at least one minimum, free, oscillatory length is provided.

Development in the field of measuring transducers of vibration-type has, in the meantime, reached a level, wherein modern measuring transducers of the described type can, for a broad application spectrum of flow measurement technology, satisfy highest requirements as regards precision and reproducibility of the measurement results. Thus, such measuring transducers are, in practice, applied for mass flow rates from some few l/h (gram per hour) up to some t/min (tons per minute), at pressures of up to 100 bar for liquids or even over 300 bar for gases. The accuracy of measurement achieved, in such case, lies usually at about 99.9% of the actual value, or above, or at a measuring error of about 0.1%, wherein a lower limit of the guaranteed measurement range can lie quite easily at about 1% of the measurement range end value. Due to the high bandwidth of their opportunities for use, industrial grade measuring transducers of vibration-type are available with nominal diameters (corresponding to the caliber of the pipeline to be connected to the measuring transducer, or to the caliber of the measuring transducer measured at the connecting flange), which lie in a nominal diameter range between 1 mm and 250 mm and at maximum nominal mass flow rate of 2200 t/h, in each case, for pressure losses of less than 1 bar. A caliber of the measuring tubes lies, in such case, for instance, in a range between 80 mm and 100 mm.

In spite of the fact that, in the meantime, measuring transducers for use in pipelines with very high mass flow rates and, associated therewith, very large calibers of far beyond 100 mm have become available, there is still considerable interest in obtaining measuring transducers of high precision and low pressure loss also for yet larger pipeline calibers, about 300 mm or more, or mass flow rates of 2500 t/h or more, for instance for applications in the petrochemical industry or in the field of transport and transfer of petroleum, natural gas, fuels, etc. This leads, in the case of correspondingly scaled enlarging of the already established measuring transducer designs known from the state of the art, especially from EP-A 1 001 254, EP-A 553 939, U.S. Pat. No. 4,793,191, US-A 2002/0157479, US-A 2007/0151368, U.S. Pat. No. 5,370,002, U.S. Pat. No. 5,796,011, U.S. Pat. No. 6,308,580, U.S. Pat. No. 6,711,958, U.S. Pat. No. 7,134,347, U.S. Pat. No. 7,350,421, or WO-A 03/027616, to the fact that the geometric dimensions would be exorbitantly large, especially the installed length corresponding to a distance between the sealing surfaces of both flanges and, in the case of curved measuring tubes, a maximum lateral extension of the measuring transducer, especially dimensions for the desired oscillation characteristics, the required load bearing ability, as well as the maximum allowed pressure loss. Along with that, also the empty mass of the measuring transducer increases unavoidably, with conventional measuring transducers of large nominal diameter already having an empty mass of about 400 kg. Investigations, which have been carried out for measuring transducers with two bent measuring tubes, constructed, for instance, according to U.S. Pat. No. 7,350,421 or U.S. Pat. No. 5,796,011, as regards their to-scale enlargement to still greater nominal diameters, have, for example, shown that, for nominal diameters of more than 300 mm, the empty mass of a to-scale enlarged, conventional measuring transducer would lie far above 500 kg, accompanied by an installed length of more than 3000 mm and a maximum lateral extension of more than 1000 mm. As a result, it can be said that industrial grade, mass producible, measuring transducers of conventional design and materials with nominal diameters far above 300 mm cannot be expected in the foreseeable future both for reasons of technical implementability, as well as also due to economic considerations.

SUMMARY OF THE INVENTION

Proceeding from the above recounted state of the art, it is consequently an object of the invention to provide a measuring transducer of high sensitivity and high oscillation quality factor, which also in the case of large mass flow rates of more than 2200 t/h, causes only a small pressure loss of less than 1 bar and which also has a construction, which is as compact as possible at large nominal diameters of over 250 mm.

For achieving the object, the invention resides in a measuring transducer of vibration-type for registering at least one physical, measured variable of a flowable medium guided in a pipeline, especially a gas, a liquid, a powder or other flowable material, and/or for producing Coriolis forces serving for registering a mass flow rate of a flowable medium guided in a pipeline, especially a gas, a liquid, a powder or other flowable material. The measuring transducer comprises, according to the invention, a, for example, essentially tubular and/or externally circularly cylindrical, transducer housing, of which an inlet-side, first housing end is formed by means of an inlet-side, first flow divider having exactly four, for example, circularly cylindrical, tapered or conical, flow openings spaced, in each case, from one another, and an outlet-side, second housing end is formed by means of an outlet-side, second flow divider having exactly four, for example, circularly cylindrical, tapered or conical, flow openings spaced, in each case, from one another. Furthermore, the measuring transducer according to the invention comprises exactly four, straight measuring tubes forming flow paths arranged for parallel flow and connected to the, for example, equally constructed, flow dividers for guiding flowing medium, especially, measuring tubes held oscillatably in the transducer housing only by means of said flow dividers and/or equally constructed and/or at least pairwise parallel relative to one another. Of the four measuring tubes of the measuring transducer of the invention, a first measuring tube, especially a circularly cylindrical, first measuring tube, opens with an inlet-side, first measuring tube end into a first flow opening of the first flow divider and with an outlet-side, second measuring tube end into a first flow opening of the second flow divider, a second measuring tube, especially a circularly cylindrical, second measuring tube, opens with an inlet-side, first measuring tube end into a second flow opening of the first flow divider and with an outlet-side, second measuring tube end into a second flow opening of the second flow divider, a third measuring tube, especially a circularly cylindrical, third measuring tube, opens with an inlet-side, first measuring tube end into a third flow opening of the first flow divider and with an outlet-side, second measuring tube end into a third flow opening of the second flow divider, and a fourth measuring tube, especially a circularly cylindrical, fourth measuring tube, opens with an inlet-side, first measuring tube end into a fourth flow opening of the first flow divider and with an outlet-side, second measuring tube end into a fourth flow opening of the second flow divider. Additionally, the measuring transducer of the invention comprises an electromechanical exciter mechanism, for example, one formed by means of an electrodynamic oscillation exciter, for producing and/or maintaining mechanical oscillations, for example, bending oscillations, of the four measuring tubes, wherein the exciter mechanism is embodied in such a manner that, therewith, the first measuring tube and the second measuring tube are excitable, during operation, to opposite phase, bending oscillations in a shared, imaginary, first plane of oscillation, and the third measuring tube and the fourth measuring tube are excitable, during operation, to opposite phase, bending oscillations in a shared, imaginary, second plane of oscillation, especially a second plane of oscillation essentially parallel to the first plane of oscillation.

In a first further development of the invention, the measuring transducer additionally comprises a first coupling element of first type, especially a plate-shaped first coupling element of first type, which is affixed at least to the first measuring tube and to the second measuring tube and spaced on the inlet side both from the first flow divider as well as also from the second flow divider for forming inlet-side, oscillation nodes at least for vibrations, especially bending oscillations, of the first measuring tube and for thereto opposite phase vibrations, especially bending oscillations, of the second measuring tube, as well as a second coupling element of first type, especially a plate-shaped second coupling element of first type and/or a second coupling element constructed equally to the first coupling element and/or a second coupling element parallel to the first coupling element, which second coupling element of first type is affixed at least to the first measuring tube and to the second measuring tube and spaced on the outlet side both from the first flow divider as well as also from the second flow divider, as well as also from the first coupling element, for forming outlet-side, oscillation nodes at least for vibrations, especially bending oscillations, of the first measuring tube and for thereto opposite phase vibrations, especially bending oscillations, of the second measuring tube.

In a first embodiment of the first further development of the invention, it is additionally provided, that all four measuring tubes are connected with one another mechanically by means of the first coupling element of first type as well as by means of the second coupling element of first type.

In a second embodiment of the first further development of the invention, it is additionally provided, that the first coupling element of first type is plate shaped, especially in such a manner, that it has essentially a rectangular, square, round, cross shaped or H-shaped basic shape.

In a third embodiment of the first further development of the invention, it is additionally provided, that the second coupling element of first type, especially a coupling element of construction equal to that of the first coupling element of first type, is plate shaped, especially in such a manner, that it has a rectangular, square, round, cross shaped or H-shaped basic shape.

In a fourth embodiment of the first further development of the invention, it is additionally provided, that the first coupling element of first type is affixed also to the third measuring tube and to the fourth measuring tube, and that the second coupling element of first type is affixed to the third measuring tube and to the fourth measuring tube.

In a fifth embodiment of the first further development of the invention, it is additionally provided, that a center of mass of the first coupling element of first type has a distance to a center of mass of the measuring transducer, which is essentially equal to a distance of a center of mass of the second coupling element of first type to said center of mass of the measuring transducer.

In a sixth embodiment of the first further development of the invention, the measuring transducer is additionally so embodied, that a free, oscillatory length, $L_{18x}$, of the first measuring tube, especially of each of the measuring tubes, corresponding to a minimum separation between the first coupling element of first type and the second coupling element of first type, amounts to less than 2500 mm, especially less than 2000 mm and/or more than 800 mm. Especially, the measuring transducer is, in such case, additionally so embodied, that each of the four measuring tubes, especially measuring tubes of equal caliber and/or equal length, has a caliber, which amounts to more than 60 mm, especially more than 80 mm, especially in such a manner, that a caliber to oscillatory length ratio of the measuring transducer, as defined by a ratio of the caliber of the first measuring tube to the free, oscillatory length of the first measuring tube, amounts to more than 0.07, especially more than 0.09 and/or less than 0.15.

In supplementation of the first further development of the invention, it is additionally provided, that the measuring transducer further comprises a third coupling element of first type, for example, a plate-shaped, third coupling element of first type, which is affixed at least to the third measuring tube and to the fourth measuring tube and spaced on the inlet side both from the first flow divider as well as also from the second flow divider, for forming inlet-side, oscillation nodes at least for vibrations, especially bending oscillations, of the third measuring tube and for thereto opposite phase vibrations, especially bending oscillations, of the fourth measuring tube, as well as a fourth coupling element of first type, for example, a plate-shaped, fourth coupling element of first type, which is affixed at least to the third measuring tube and to the fourth measuring tube and spaced on the outlet side both from the first flow divider as well as also from the second flow divider, as well as also from the third coupling element of first type, for forming outlet-side, oscillation nodes at least for vibrations, especially bending oscillations, of the third measuring tube and for thereto opposite phase vibrations, especially bending oscillations, of the fourth measuring tube. In such case, for example, also all four measuring tubes can be connected with one another mechanically by means of the third coupling element of first type as well as by means of the fourth coupling element of first type.

In a second further development of the invention, the measuring transducer additionally comprises a first coupling element of second type, for example, a plate shaped or rod shaped, first coupling element of second type, which is affixed to the first measuring tube and to the third measuring tube, but otherwise to no others of the measuring tubes, and which is spaced both from the first coupling element of first type as well as also from the second coupling element of first type for synchronizing vibrations, especially bending oscillations, of the first measuring tube and thereto equal frequency vibrations, especially bending oscillations, of the third measuring tube, as well as a second coupling element of second type, for example, a plate shaped or rod shaped, second coupling element of second type, which is affixed to the second measuring tube and to the fourth measuring tube, but otherwise to no others of the measuring tubes, and which is spaced both from the first coupling element of first type as well as also from the second coupling element of first type, as well as also from the first coupling element of second type, especially in such a manner, that the first and second coupling elements of second type are placed in the measuring transducer lying opposite one another, for synchronizing vibrations, especially bending oscillations, of the second measuring tube and thereto equal frequency vibrations, especially bending oscillations, of the fourth measuring tube. In supplementation thereof, the measuring transducer can further comprise a third coupling element of second type, for example, a plate shaped or rod shaped, third coupling element of second type, which is affixed to the first measuring tube and to the third measuring tube, but otherwise to no others of the measuring tubes, and which is spaced from the first coupling element of second type, for synchronizing vibrations, especially bending oscillations, of the first measuring tube and thereto equal frequency vibrations, especially bending oscillations, of the third measuring tube, as well as a fourth coupling element of second type, for example, a plate shaped or rod shaped, fourth coupling element of second type, which is affixed to the second measuring tube and to the fourth measuring tube, but otherwise to no others of the measuring tubes, and which is spaced, in each case, from the second and third coupling elements of second type, especially in such a manner, that the third and fourth coupling elements of second type are placed lying opposite one another in the measuring transducer, for synchronizing vibrations, especially bending oscillations, of the second measuring tube and thereto equal frequency vibrations, especially bending oscillations, of the fourth measuring tube.

Moreover, the measuring transducer can comprise, additionally, a fifth coupling element of second type, for example, a plate shaped or rod shaped, fifth coupling element of second type, which is affixed to the first measuring tube and to the third measuring tube, but otherwise to no others of the measuring tubes, and which is spaced from the first and third coupling elements of second type, for synchronizing vibrations, especially bending oscillations, of the first measuring tube and thereto equal frequency vibrations, especially bending oscillations, of the third measuring tube, as well as a, for example, a plate shaped or rod shaped, sixth coupling element of second type, which is affixed to the second measuring tube and to the fourth measuring tube, but otherwise to no others of the measuring tubes, and which is spaced, in each case, from the second, fourth and fifth coupling elements of second type, especially in such a manner that the fifth and sixth coupling elements of second type are placed in the measuring transducer lying opposite one another, for synchronizing vibrations, especially bending oscillations, of the second measuring tube and thereto equal frequency vibrations, especially bending oscillations, of the fourth measuring tube.

In a first embodiment of the invention, it is additionally provided, that each of the four measuring tubes, especially measuring tubes of equal caliber and/or equal length, has a caliber, which amounts to more than 60 mm, especially more than 80 mm.

In a second embodiment of the invention, it is additionally provided, that the first flow divider has a flange, especially a flange having mass of more than 50 kg, for connecting the measuring transducer to a tubular segment of the pipeline serving for supplying medium to the measuring transducer and the second flow divider has a flange, especially a flange having a mass of more than 50 kg, for connecting the measuring transducer to a segment of the pipeline serving for removing medium from the measuring transducer. Developing this embodiment of the invention further, each of the flanges has a sealing surface for fluid tight connecting of the measuring transducer with the, in each case, corresponding tubular segment of the pipeline, wherein a distance between the sealing surfaces of both flanges defines an installed length of the measuring transducer, especially an installed length amounting to more than 1200 mm and/or less than 3000 mm. Especially, the measuring transducer is additionally so embodied, that, in such case, a measuring tube length of the first measuring tube corresponding to a minimum separation between the first flow opening of the first flow divider and the first flow opening of the second flow divider is so selected, that a measuring tube length to installed length ratio of the measuring transducer, as defined by a ratio of the measuring tube length of the first measuring tube to the installed length of the measuring transducer, amounts to more than 0.7, especially more than 0.8 and/or less than 0.95, and/or that a caliber to installed length ratio of the measuring transducer, as defined by a ratio of the caliber of the first measuring tube to the installed length of the measuring transducer, amounts to more than 0.02, especially more than 0.05 and/or less than 0.09. Alternatively thereto or in supplementation thereof, the measuring transducer is so embodied, that a nominal diameter to installed length ratio of the measuring transducer, as defined by a ratio of the nominal diameter of the measuring transducer to the installed length of the measuring transducer, is smaller than 0.3, especially smaller than 0.2 and/or greater than 0.1, wherein the nominal diameter corresponds to a caliber of the pipeline, in whose course the measuring transducer is to be used.

In a third embodiment of the invention, it is additionally provided, that a measuring tube length of the first measuring tube corresponding to a minimum separation between the first flow opening of the first flow divider and the first flow opening of the second flow divider amounts to more than 1000 mm, especially more than 1200 mm and/or less than 2000 mm.

In a fourth embodiment of the invention, it is additionally provided, that each of the four measuring tubes, especially four measuring tubes of equal caliber, is so arranged, that a smallest lateral separation of each of the four measuring tubes, especially measuring tubes of equal length, from a housing side wall of the transducer housing is, in each case, greater than zero, especially greater than 3 mm and/or greater than twice a respective tube wall thickness; and/or that a smallest lateral separation between two neighboring measuring tubes amounts to, in each case, greater than 3 mm and/or greater than the sum of their respective tube wall thicknesses.

In a fifth embodiment of the invention, it is additionally provided, that each of the flow openings is so arranged, that a smallest lateral separation of each of the flow openings from a housing side wall of the transducer housing amounts, in each case, to greater than zero, especially greater than 3 mm and/or greater than twice a smallest tube wall thickness of the measuring tubes; and/or that a smallest lateral separation between the flow openings amounts to greater than 3 mm and/or greater than twice a smallest tube wall thickness of the measuring tubes.

In a third further development of the invention, the measuring transducer additionally comprises a plurality of annular stiffening elements, especially equally constructed stiffening elements, serving for increasing the oscillation quality factor of the measuring tubes. Each of the stiffening elements is so placed on exactly one of the measuring tubes that it grips around such along one of the peripheral lines of the measuring tube. According to an embodiment of the third further development of the invention, there are placed on each of the measuring tubes at least four annular stiffening elements, for example, equally constructed stiffening elements, especially in such a manner, that the stiffening elements are so placed in the measuring transducer, that two adjoining stiffening elements mounted on the same measuring tube have, relative to one another, a separation, which amounts to at least 70% of a tube outer diameter of said measuring tube, at most, however, 150% of such tube outer diameter, for example, a separation in the range of 80% to 120% of such tube outer diameter.

In a fourth further development of the invention, the measuring transducer additionally comprises a sensor arrangement for producing oscillation measurement signals representing vibrations, especially bending oscillations, of the measuring tubes, by reacting to vibrations of the measuring tubes, especially bending oscillations excited by means of the exciter mechanism. The sensor arrangement is, for example, an electrodynamic sensor arrangement and/or is formed by means of oscillation sensors constructed equally to one another.

In a first embodiment of the fourth further development of the invention, it is provided, that the sensor arrangement is formed by means of an inlet-side, first oscillation sensor, especially an electrodynamic, first oscillation sensor and/or a first oscillation sensor differentially registering oscillations of the first measuring tube relative to the second measuring tube, as well as by means of an outlet-side, second oscillation sensor, especially an electrodynamic, second oscillation sensor and/or a second oscillation sensor differentially registering oscillations of the first measuring tube relative to the second measuring tube, especially in such a manner that a measuring length of the measuring transducer corresponding to a minimum separation between the first oscillation sensor and the second oscillation sensor amounts to more than 500 mm, especially more than 600 mm and/or less than 1200 mm, and/or in such a manner that a caliber to measuring length ratio of the measuring transducer, as defined by a ratio of a caliber of the first measuring tube to the measuring length of the measuring transducer, amounts to more than 0.05, especially more than 0.09. Additionally, the first oscillation sensor can be formed by means of a permanent magnet held on the first measuring tube and a cylindrical coil permeated by the magnetic field of the permanent magnet and held on the second measuring tube, and the second oscillation sensor by means of a permanent magnet held on the first measuring tube and a cylindrical coil permeated by the magnetic field of the permanent magnet and held on the second measuring tube.

In a second embodiment of the fourth further development of the invention, it is additionally provided, that the sensor arrangement is formed by means of an inlet-side, first oscillation sensor, especially an electrodynamic, first oscillation sensor and/or a first oscillation sensor differentially registering oscillations of the first measuring tube relative to the second measuring tube, by an outlet-side, second oscillation sensor, especially an electrodynamic, second oscillation sensor and/or a second oscillation sensor differentially registering oscillations of the first measuring tube relative to the second measuring tube, by an inlet-side, third oscillation sensor, especially an electrodynamic, third oscillation sensor and/or a third oscillation sensor differentially registering oscillations of the third measuring tube relative to the fourth measuring tube, as well as by an outlet-side, fourth oscillation sensor, especially an electrodynamic, fourth oscillation sensor and/or a fourth oscillation sensor differentially registering oscillations of the third measuring tube relative to the fourth measuring tube, especially in such a manner, that a measuring length of the measuring transducer corresponding to a minimum separation between the first oscillation sensor and the second oscillation sensor amounts to more than 500 mm, especially more than 600 mm and/or less than 1200 mm, and/or in such a manner that a caliber to measuring length ratio of the measuring transducer, as defined by a ratio of a caliber of the first measuring tube to the measuring length of the measuring transducer, amounts to more than 0.05, especially more than 0.09. In such case, in advantageous manner, the first and third oscillation sensors can be interconnected electrically in series in such a manner, that a combined oscillation measurement signal represents combined inlet-side oscillations of the first and third measuring tubes relative to the second and fourth measuring tube, and/or the second and fourth oscillation sensors can be interconnected electrically in series in such a manner, that a combined oscillation measurement signal represents combined outlet-side oscillations of the first and third measuring tubes relative to the second and fourth measuring tube. Alternatively or in supplementation, the first oscillation sensor can further be formed by means of a permanent magnet held on the first measuring tube and a cylindrical coil permeated by the magnetic field of the permanent magnet and held on the second measuring tube, and the second oscillation sensor by means of a permanent magnet held on the first measuring tube and a cylindrical coil permeated by the magnetic field of the permanent magnet and held on the second measuring tube, and/or the third oscillation sensor by means of a permanent magnet held on the third measuring tube and a cylindrical coil permeated by the magnetic field of the permanent magnet and held on the fourth measuring tube and the fourth oscillation sensor by means of a permanent magnet held on the third measuring tube and a cylindrical coil permeated by the magnetic field of the permanent magnet and held on the fourth measuring tube.

In a sixth embodiment of the invention, it is additionally provided, that a mass ratio of an empty mass of the total measuring transducer to an empty mass of the first measuring tube is greater than 10, especially greater than 15 and smaller than 25.

In a seventh embodiment of the invention, it is additionally provided, that an empty mass, $M_{18}$, of the first measuring tube, especially each of the measuring tubes, is greater than 20 kg, especially greater than 30 kg and/or smaller than 50 kg.

According to an eighth embodiment of the invention, it is additionally provided, that an empty mass of the measuring transducer is greater than 200 kg, especially greater than 300 kg.

In a ninth embodiment of the invention, it is additionally provided, that a nominal diameter of the measuring transducer, which corresponds to a caliber of the pipeline, in whose course the measuring transducer is to be used, amounts to more than 100 mm, especially greater than 300 mm. In advantageous manner, the measuring transducer is additionally so embodied, that a mass to nominal diameter ratio of the measuring transducer, as defined by a ratio of the empty mass of the measuring transducer to the nominal diameter of the measuring transducer, is smaller than 2 kg/mm, especially smaller than 1 kg/mm and/or greater than 0.5 kg/mm.

In a tenth embodiment of the invention, it is additionally provided, that the first and the second measuring tubes are of equal construction, at least as regards a material, of which their tube walls are, in each case, composed, and/or as regards their geometrical tube dimensions, especially a tube length, a tube wall thickness, a tube outer diameter and/or a caliber.

According to an eleventh embodiment of the invention, it is additionally provided, that the third and fourth measuring tubes are of equal construction, at least as regards a material, of which their tube walls are, in each case, composed, and/or as regards their geometric tube dimensions, especially a tube length, a tube wall thickness, a tube outer diameter and/or a caliber.

In a twelfth embodiment of the invention, it is additionally provided, that the four measuring tubes are of equal construction, as regards a material, of which their tube walls are composed, and/or as regards their geometric tube dimensions, especially a tube length, a tube wall thickness, a tube outer diameter and/or a caliber. It can, however, also be of advantage, when, alternatively thereto, both the third measuring tube as well as also the fourth measuring tube are different from the first measuring tube and from the second measuring tube as regards their respective geometric tube dimensions, especially a tube length, a tube wall thickness, a tube outer diameter and/or a caliber.

In a thirteenth embodiment of the invention, it is additionally provided, that a material, of which the tube walls of the four measuring tubes are at least partially composed, is titanium and/or zirconium and/or duplex steel and/or super duplex steel.

In a fourteenth embodiment of the invention, it is additionally provided, that the transducer housing, the flow dividers and tube walls of the measuring tubes are, in each case, composed of steel, for example, stainless steel.

In a fifteenth embodiment of the invention, it is additionally provided, that the minimum bending oscillation, resonance frequencies at least of the first and second measuring tubes are essentially equal and the minimum bending oscillation, resonance frequencies at least of the third and fourth measuring tubes are essentially equal. In such case, the minimum bending oscillation, resonance frequencies of all four measuring tubes can be essentially equal or, however, also kept only pairwise equal.

In a sixteenth embodiment of the invention, it is additionally provided, that the four flow openings of the first flow divider are so arranged, that imaginary areal centers of gravity associated with the cross sectional areas, especially circularly shaped cross sectional areas, of the flow openings of the first flow divider form the vertices of an imaginary square, wherein such cross sectional areas lie in a shared, imaginary cutting plane of the first flow divider extending perpendicularly to a longitudinal axis of the measuring transducer, especially a longitudinal axis parallel to a principal flow axis of the measuring transducer.

In a seventeenth embodiment of the invention, it is additionally provided, that the four flow openings of the second flow divider are so arranged, that imaginary areal centers of gravity associated with the cross sectional areas, especially circularly shaped cross sectional areas, of the flow openings of the second flow divider form the vertices of an imaginary square, wherein such cross sectional areas lie in a shared, imaginary cutting plane of the second flow divider extending perpendicularly to a longitudinal axis of the measuring transducer, especially a longitudinal axis parallel to a principal flow axis of the measuring transducer.

According to an eighteenth embodiment of the invention, it is additionally provided, that the exciter mechanism is formed by means of a first oscillation exciter, especially an electrodynamic, first oscillation exciter and/or a first oscillation exciter differentially exciting oscillations of the first measuring tube relative to the second measuring tube.

Especially, the exciter mechanism, according to a first further development of the eighteenth embodiment of the invention, is formed by means of a second oscillation exciter, for example, an electrodynamic second oscillation exciter and/or a second oscillation exciter differentially exciting oscillations of the third measuring tube relative to the fourth measuring tube. In such case, it is additionally provided, that the first and second oscillation exciters are interconnected electrically in series, in such a manner, that a combined driver signal excites combined oscillations of the first and third measuring tubes relative to the second and fourth measuring tube. The oscillation exciter of the exciter mechanism can be formed, for example, by means of a permanent magnet held on the first measuring tube and a cylindrical coil permeated by the magnetic field of the permanent magnet and held on the second measuring tube, and wherein the second oscillation exciter is formed by means of a permanent magnet held on the third measuring tube and a cylindrical coil permeated by the magnetic field of the permanent magnet and held on the fourth measuring tube.

In a second further development of the eighteenth embodiment of the invention, the measuring transducer further comprises: A first plate shaped stiffening element, which is affixed to the first measuring tube and to the third measuring tubes, and, indeed, affixed to segments of the first and third measuring tubes lying, respectively, between the first oscillation exciter and the first flow divider, for tuning resonance frequencies of bending oscillations of the first measuring tube and the third measuring tube in a third plane of oscillation essentially perpendicular to the first and/or second planes of oscillation; a second plate shaped stiffening element, which is affixed to the second measuring tube and to the fourth measuring tubes, and, indeed, affixed to segments of the second and fourth measuring tubes lying, respectively, between the first oscillation exciter and the first flow divider, for tuning resonance frequencies of bending oscillations of the second measuring tube and the fourth measuring tube in a fourth plane of oscillation essentially perpendicular to the first and/or second planes of oscillation; a third plate-shaped stiffening element, which is affixed to the first measuring tube and to the third measuring tube, and, indeed, affixed to segments of the first and third measuring tubes lying, respectively, between the first oscillation exciter and the second flow divider, for tuning resonance frequencies of bending oscillations of the first measuring tube and the third measuring tubes in the third plane of oscillation; as well as a fourth plate-shaped stiffening element, which is affixed to the second measuring tube and to the fourth measuring tubes, and, indeed, affixed to segments of the second and fourth measuring tubes lying, respectively, between the first oscillation exciter and the second flow divider, for tuning resonance frequencies of bending oscillations of the second measuring tube and the fourth measuring tube in the fourth plane of oscillation.

The plate shaped stiffening elements can, for the case in which the sensor arrangement is formed by means of an inlet-side, first oscillation sensor and by means of an outlet-side, second oscillation sensor, be arranged in the measuring transducer e.g. in such a manner that the first plate shaped stiffening element is affixed to the segment of the first measuring tube between the first oscillation sensor and the first flow divider along one of the straight lateral surface elements of the segment, for instance that nearest the third measuring tube, as well as to the segment of the third measuring tube lying between the first oscillation sensor and the first flow divider along one of the straight lateral surface elements of the segment, for instance that nearest the first measuring tube, the second plate shaped stiffening element is affixed to the segment of the second measuring tube lying between the first oscillation sensor and the first flow divider along one of the straight lateral surface elements of the segment, for instance that nearest the fourth measuring tube, as well as to the segment of the fourth measuring tube lying between the first oscillation sensor and the first flow divider along one of the straight lateral surface elements of the segment, for instance that nearest the second measuring tube, the third plate shaped stiffening element is affixed to the segment of the first measuring tube lying between the second oscillation sensor and the second flow divider along one of the straight lateral surface elements of the segment, for instance that nearest the third measuring tube, as well as to the segment of the third measuring tube lying between the second oscillation sensor and the second flow divider along one of the straight lateral surface elements of the segment, for instance that nearest the first measuring tube, and the fourth plate shaped stiffening element is affixed to the segment of the second measuring tube lying between the second oscillation sensor and the second flow divider along one of the straight lateral surface elements of the segment, for instance that nearest the fourth measuring tube, as well as to the segment of the fourth measuring tube lying between the second oscillation sensor and the second flow divider along one of the straight lateral surface elements of the segment, for instance that nearest the second measuring tube. Additionally, it is provided in such case that each of the four plate shaped stiffening elements, for instance plate shaped stiffening elements of equal construction to one another, is, in each case, so embodied and so placed in the measuring transducer that it has a height corresponding to a smallest distance between the lateral surface elements of each two measuring tubes along which it is, in each case, fixed, especially a height which is smaller by more than half than a length of said plate shaped stiffening element measured in the direction of said lateral surface elements. In supplementation thereto, each of the four plate shaped stiffening elements can further, in each case, be so embodied that the length of each of the plate shaped stiffening elements is greater, especially two times greater, than a breadth of said plate shaped stiffening element.

In a nineteenth embodiment of the invention, it is additionally provided, that a middle segment of the transducer housing is formed by means of a straight tube, for example, a circularly cylindrical, straight tube.

In a twentieth embodiment of the invention, it is additionally provided, that the transducer housing is essentially tubularly embodied, for example, circularly cylindrically embodied. In such case, it is additionally provided, that the transducer housing has a largest housing inner diameter, which is greater than 150 mm, especially greater than 250 mm, especially in such a manner, that a housing to measuring tube inner diameter ratio of the measuring transducer, as defined by a ratio of the largest housing inner diameter to a caliber of the first measuring tube is kept greater than 3, especially greater than 4 and/or smaller than 5, and/or that a housing inner diameter to nominal diameter ratio of the measuring transducer, as defined by a ratio of the largest housing inner diameter to the nominal diameter of the measuring transducer is smaller than 1.5, especially smaller than 1.2 and/or greater than 0.9, wherein the nominal diameter corresponds to a caliber of the pipeline, in whose course the measuring transducer is to be used. The housing inner diameter to nominal diameter ratio of the measuring transducer can, in such case, in advantageous manner, be, for example, also equal to one.

Moreover, the invention resides in an in-line measuring device for measuring a density and/or a mass flow rate, especially also a total mass flow totaled over a time interval, of a medium, especially of a gas, a liquid, a powder or other flowable material flowing in a pipeline, at least at times, especially with a mass flow rate of more than 2200 t/h, which in-line measuring device, especially an in-line measuring device embodied as a compact device, comprises one of the aforementioned measuring transducers as well as a measuring device electronics electrically coupled with the measuring transducer, especially also a measuring device electronics mechanically rigidly connected with the measuring transducer.

A basic idea of the invention is to use, instead of the two measuring tubes, through which the medium flows in parallel, as used in the case of conventional measuring transducers of large nominal diameter, four straight measuring tubes, through which the medium flows in parallel, and so, on the one hand, to enable an optimal exploitation of the limited offering of space, while, on the other hand, being able to assure an acceptable pressure loss over a broad measuring range, especially also in the case of very high, mass flow rates of far over 2200 t/h. Moreover, the effective flow cross section of the inner part resulting from the total cross section of the four measuring tubes can, in comparison to conventional measuring transducers of equal nominal diameter and equal empty mass having only two measuring tubes, be directly increased by more than 20%.

An advantage of the measuring transducer of the invention resides additionally in the fact that predominantly established, structural designs, such as regards materials used, joining technology, manufacturing steps, etc., can be applied, or must only be slightly modified, whereby also manufacturing costs are, in total, quite comparable to those of conventional measuring transducers. As a result, a further advantage of the invention is to be found in the fact that, thereby, not only an opportunity is created for implementing comparatively compact measuring transducers of vibration-type also with large nominal diameters of over 150 mm, especially with a nominal diameter of larger 250 mm, with manageable geometric dimensions and empty dimensions, but, additionally, also, this can be accomplished in an economically sensible manner.

The measuring transducer of the invention is, consequently, especially suitable for measuring flowable media guided in a pipeline having a caliber of larger 150 mm, especially of 300 mm or greater. Additionally, the measuring transducer is also suitable for measuring also mass flows, which are, at least at times, greater than 2200 t/h, especially, at least at times, amounting to more than 2400 t/h, such as can occur e.g. in the case of applications for measuring petroleum, natural gas or other petrochemical materials.

BRIEF DESCRIPTION OF THE DRAWINGS

The invention, as well as other advantageous embodiments thereof, will now be explained in greater detail on the basis of examples of embodiments presented in the figures of the drawing. Equal parts are provided in the figures with equal reference characters; when required to avoid clutter or when it otherwise appears sensible, already mentioned reference characters are omitted in subsequent figures. Other advantageous embodiments or further developments, especially also combinations of first only individually explained aspects of the invention, will become evident additionally from the figures of the drawing, as well as also alone from the dependent claims.

In particular, the figures of the drawing show as follows:

FIGS. 6a, and 6b projections of an inner part of the measuring transducer of FIG. 4 in two different side views;

FIG. 7 in perspective, side view, a further development of the measuring transducer of FIG. 4, installed in an in-line measuring device of FIG. 1.

DETAILED DISCUSSION IN CONJUNCTION WITH THE DRAWINGS

Figure 1:
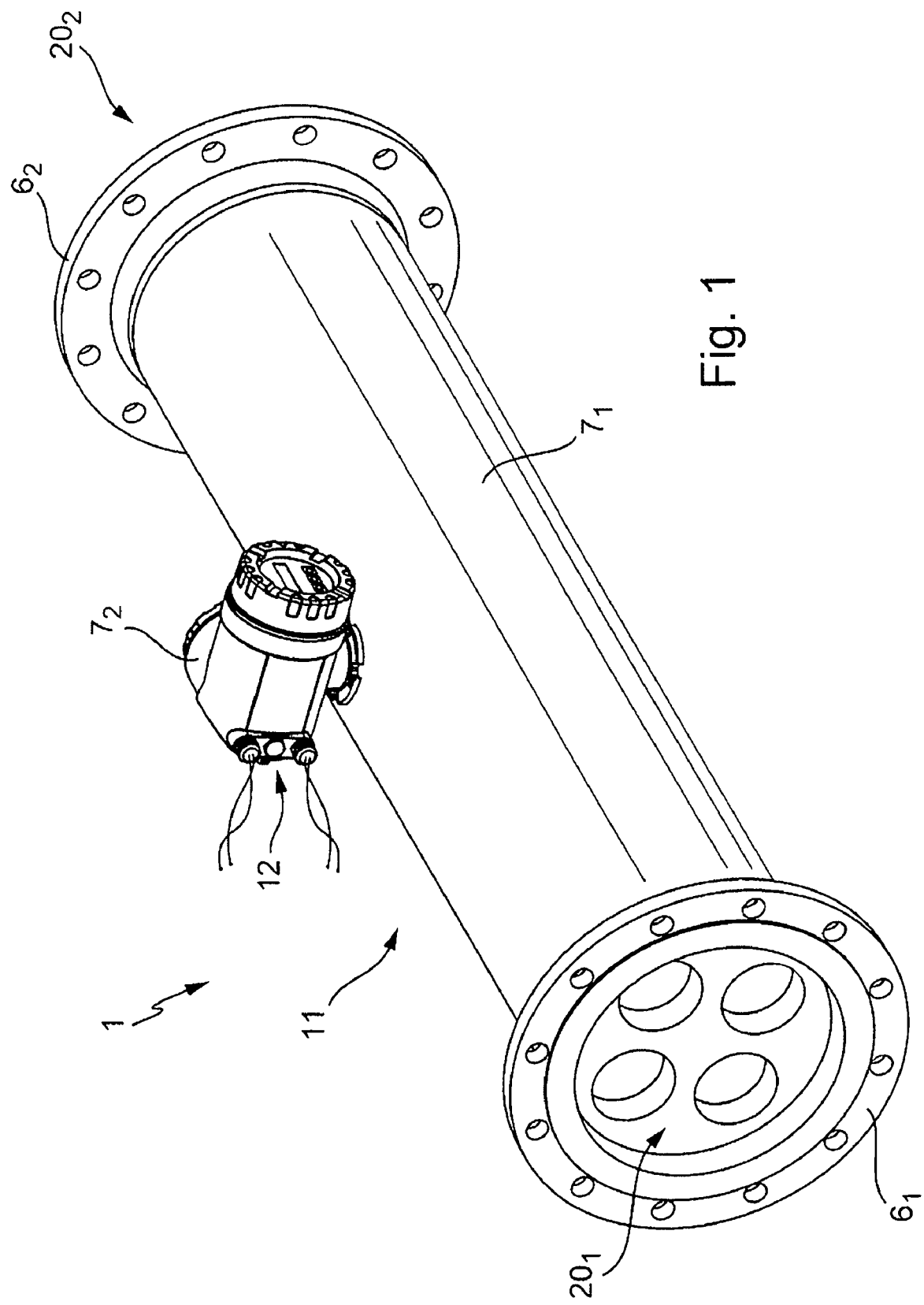
FIGS. 1, and 2 an in-line measuring device serving, for example, as a Coriolis flow/density/viscosity transducer, in perspective, also partially sectioned, side views.
Figure 2:
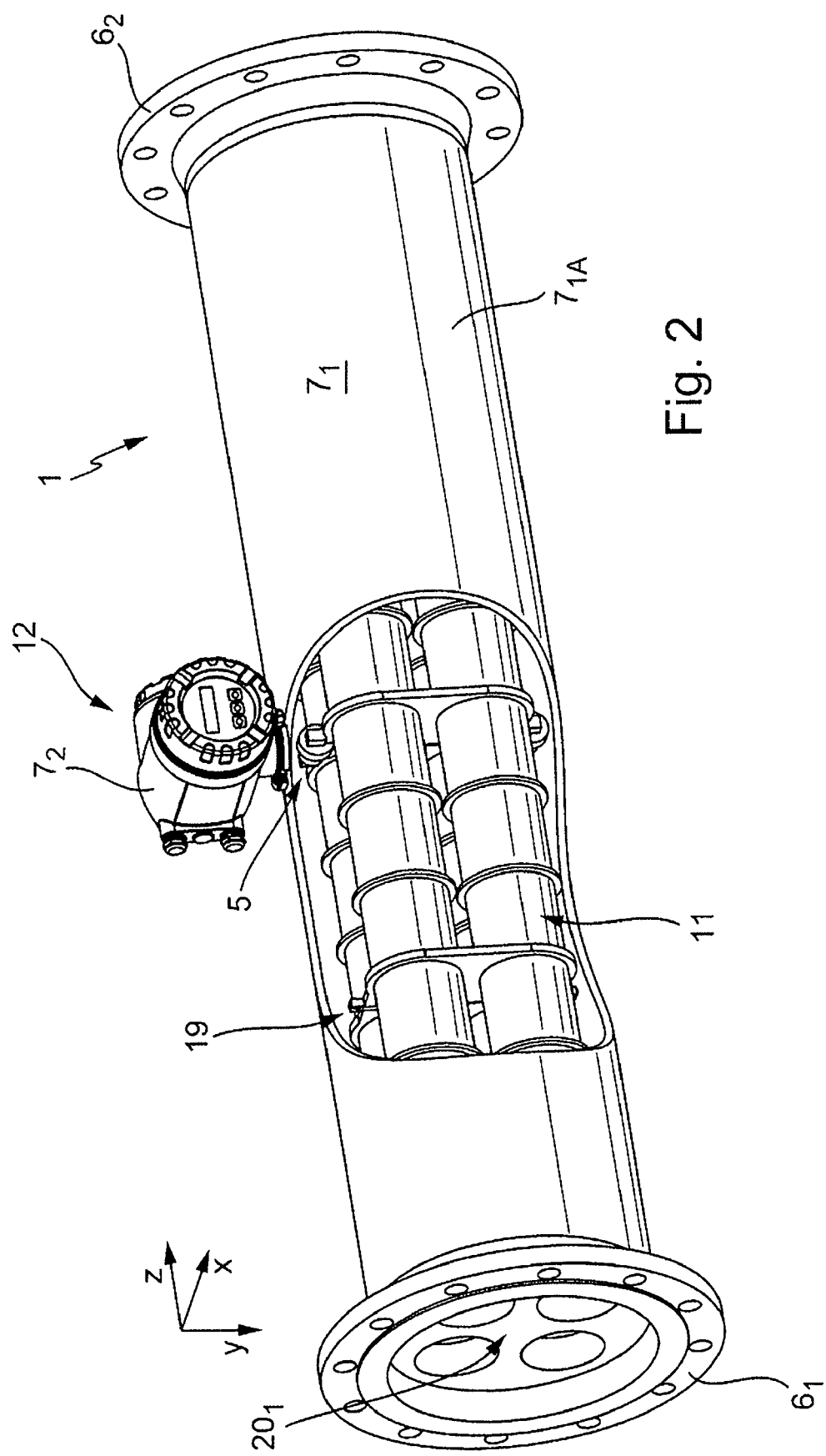

FIGS. 1, 2 show, schematically, an in-line measuring device 1, especially an in-line measuring device embodied as a Coriolis, mass flow, and/or density, measuring device, which serves for registering a mass flow m of a medium flowing in a pipeline (not shown) and for representing such in a mass flow, measured value representing this mass flow instantaneously. The medium can be practically any flowable material, for example, a powder, a liquid, a gas, a vapor, or the like. Alternatively or in supplementation, the in-line measuring device 1 can, in given cases, also be used for measuring a density $\rho$ and/or a viscosity $\eta$ of the medium. Especially, the in-line measuring device is provided for measuring media, such as e.g. petroleum, natural gas or other petrochemical materials, which are flowing in a pipeline having a caliber greater than 250 mm, especially a caliber of 300 mm or more. Especially, the in-line measuring device is additionally provided for measuring flowing media of the aforementioned type, which are caused to flow with a mass flow rate of greater than 2200 t/h, especially greater than 2500 t/h.

The in-line measuring device 1 comprises, for such purpose: A measuring transducer 11 of vibration-type, through which the medium being measured flows, during operation; as well as, electrically connected with the measuring transducer 11, a measuring device electronics 12, which is here not shown in detail, but, instead only schematically in the form of a contained unit. In advantageous manner, the measuring device electronics 12 is so designed that, during operation of the in-line measuring device 1, it can exchange measuring, and/or other operating, data with a measured value processing unit superordinated to it, for example, a programmable logic controller (PLC), a personal computer and/or a work station, via a data transmission system, for example, a hardwired fieldbus system and/or wirelessly per radio. Furthermore, the measuring device electronics 12 is so designed, that it can be fed by an external energy supply, for example, also via the aforementioned fieldbus system. For the case, in which the in-line measuring device 1 is provided for coupling to a fieldbus, or other communication, system, the measuring device electronics 12, especially a programmable measuring device electronics, includes, additionally, a corresponding communication interface for data communication, e.g. for sending the measured data to the already mentioned, programmable logic controller or a superordinated process control system.

FIGS. 4, 5a, 5b, 6a, 6b, 7, 8a, 8b show different representations of examples of embodiments for a measuring transducer 11 of vibration-type suited for the in-line measuring device 1, especially one serving as a Coriolis, mass flow, density and/or viscosity, transducer, which measuring transducer 11 is applied, during operation, in the course of a pipeline (not shown), through which a medium to be measured, for example, a powdered, liquid, gaseous or vaporous medium, is flowing. The measuring transducer 11 serves to produce, as already mentioned, in a medium flowing therethrough, such mechanical reaction forces, especially Coriolis forces dependent on mass flow, inertial forces dependent on density of the medium and/or frictional forces dependent on viscosity of the medium, which react measurably, especially registerably by sensor, on the measuring transducer. Derived from these reaction forces describing the medium, by means of evaluating methods correspondingly implemented in the measuring device electronics in manner known to those skilled in the art, e.g. the mass flow, the density and/or the viscosity of the medium can be measured.

The measuring transducer 11 includes a transducer housing $7_1$, which is, here, essentially tubular, and externally circularly cylindrical, and which serves, among other things, also as a support frame, in which other components of the measuring transducer 11 serving for registering the at least one measured variable are accommodated to be protected against external, environmental influences. In the example of an embodiment shown here, at least one middle segment of the transducer housing $7_1$ is formed by means of a straight, especially circularly cylindrical, tube, so that, for manufacture of the transducer housing, for example, also cost effective, welded or cast, standard tubes, for example, of cast steel or forged steel, can be used.

An inlet-side, first housing end of the transducer housing $7_1$ is formed by means of an inlet-side, first flow divider $20_1$ and an outlet-side, second housing end of the transducer housing $7_1$ is formed by means of outlet-side, second flow divider $20_2$. Each of the two flow dividers $20_1$, $20_2$, which are, in this respect, formed as integral components of the housing, includes exactly four, for example, circularly cylindrical or tapered or conical, flow openings $20_{1A}$, $20_{1B}$, $20_{1C}$, $20_{1D}$, or $20_{2A}$, $20_{2B}$, $20_{2C}$, $20_{2D}$, each spaced from one another and/or each embodied as an inner cone.

Moreover, each of the flow dividers $20_1$, $20_2$, for example, manufactured of steel, is provided with a flange $6_1$, or $6_2$, for example, manufactured of steel, for connecting of the measuring transducer 11 to a tubular segment of the pipeline serving for supplying medium to the measuring transducer, or to a tubular segment of such pipeline serving for removing medium from the measuring transducer. Each of the two flanges $6_1$, $6_2$ has, according to an embodiment of the invention, a mass of more than 50 kg, especially more than 60 kg and/or less than 100 kg. For leakage free, especially fluid tight, connecting of the measuring transducer with the, in each case, corresponding tubular segment of the pipeline, each of the flanges includes additionally, in each case, a corresponding, as planar as possible, sealing surface $6_{1A}$, or $6_{2A}$. A distance between the two sealing surfaces $6_{1A}$, $6_{2A}$ of both flanges defines, thus, for practical purposes, an installed length, $L_{11}$, of the measuring transducer 11. The flanges are dimensioned, especially as regards their inner diameter, their respective sealing surface as well as the flange bores serving for accommodating corresponding connection bolts, according to the nominal diameter $D_{11}$ provided for the measuring transducer 11 as well as the therefor, in given cases, relevant industrial standards, corresponding to a caliber of the pipeline, in whose course the measuring transducer is to be used.

As a result of the large nominal diameter lastly desired for the measuring transducer, its installed length $L_{11}$ amounts, according to an embodiment of the invention, to more than 1200 mm. Additionally, it is, however, provided that the installed length of the measuring transducer 11 is kept as small as possible, especially smaller than 3000 mm. The flanges $6_1$, $6_2$ can, as well as also directly evident from FIG. 4 and such as quite usual in the case of such measuring transducers, be arranged, for this purpose, as near as possible to the flow openings of the flow dividers $20_1$, $20_2$, in order so to provide an as short as possible inlet, or outlet, as the case may be, region in the flow dividers and, thus, in total, to provide an as short as possible installed length $L_{11}$ of the measuring transducer, especially an installed length $L_{11}$ of less than 3000 mm. For an as compact as possible measuring transducer with an also in the case of desired high mass flow rates of over 2200 t/h, according to another embodiment of the invention, the installed length and the nominal diameter of the measuring transducer are so dimensioned, matched to one another, that a nominal diameter to installed length ratio $D_{11}/L_{11}$ of the measuring transducer, as defined by a ratio of the nominal diameter $D_{11}$ of the measuring transducer to the installed length $L_{11}$ of the measuring transducer is smaller than 0.3, especially smaller than 0.2 and/or greater than 0.1.

In an additional embodiment of the measuring transducer, the transducer housing comprises an essentially tubular, middle segment. Additionally, it is provided that the transducer housing is so dimensioned, that a housing inner diameter to nominal diameter ratio of the measuring transducer defined by a ratio of the largest housing inner diameter to the nominal diameter of the measuring transducer is, indeed, greater than 0.9, however, smaller than 1.5, as much as possible, however, smaller than 1.2.

In the case of the here illustrated example of an embodiment, there adjoin on the inlet and outlet sides of the middle segment, additionally, likewise tubular end segments of the transducer housing. For the case illustrated in the example of an embodiment, in which the middle segment and the two end segments, as well as also the flow dividers connected with the respective flanges in the inlet and outlet regions all have the same inner diameter, the transducer housing can in advantageous manner also be formed by means of a one piece, for example, cast or forged, tube, on whose ends the flanges are formed or welded, and in the case of which the flow dividers are formed by means of plates having the flow openings, especially plates somewhat spaced from the flanges and welded to the inner wall orbitally and/or by means of laser. Especially for the case, in which the mentioned housing inner diameter to nominal diameter ratio of the measuring transducer is selected equal to one, for manufacture of the transducer housing, for example, a tube matched to the pipeline to be connected to as regards caliber, wall thickness and material and, in that respect, also as regards the allowed operating pressure and having a length correspondingly matching the selected measuring tube length can be used. For simplifying the transport of the measuring transducer, or the totally therewith formed, in-line measuring device, additionally, such as, for example, also provided in the initially mentioned U.S. Pat. No. 7,350,421, transport eyes can be provided affixed on the inlet side and on the outlet side externally on the transducer housing.

For conveying the medium flowing, at least at times, through pipeline and measuring transducer, the measuring transducer of the invention comprises, additionally, exactly four, straight, measuring tubes $18_1$, $18_2$, $18_3$, $18_4$ held oscillatably in the transducer housing 10, especially measuring tubes $18_1$, $18_2$, $18_3$, $18_4$, which are parallel relative to one another and/or equally long, which, during operation, in each case, communicate with the pipeline and, at least at times, are caused to vibrate in at least one oscillatory mode, the so-called wanted mode, suited for ascertaining the physical, measured variable. Especially suited as wanted mode and naturally inherent to each of the measuring tubes $18_1$, $18_2$, $18_3$, and $18_4$ is a bending oscillation, fundamental mode, which at a minimum bending oscillation, resonance frequency, $f18_1$, $f18_2$, $f18_3$, or $f18_4$, has exactly one oscillatory antinode.

Of the four—here essentially circularly cylindrical, of equal length and parallel relative to one another as well as to the above mentioned, middle tubular segment of the transducer housing—measuring tubes, a first measuring tube $18_1$ opens with an inlet-side, first measuring tube end into a first flow opening $20_{1A}$ of the first flow divider $20_1$ and with an outlet-side, second measuring tube end into a first flow opening $20_{2A}$ of the second flow divider $20_2$, a second measuring tube $18_2$ opens with an inlet-side, first measuring tube end into a second flow opening $20_{1B}$ of the first flow divider $20_1$ and with an outlet-side, second measuring tube end into a second flow opening $20_{2B}$ of the second flow divider $20_2$, a third measuring tube $18_3$ opens with an inlet-side, first measuring tube end into a third flow opening $20_{1C}$ of the first flow divider $20_1$ and with an outlet-side, second measuring tube end into a third flow opening $20_{2C}$ of the second flow divider $20_2$ and a fourth measuring tube $18_4$ opens with an inlet-side, first measuring tube end into a fourth flow opening $20_{1D}$ of the first flow divider $20_1$ and with an outlet-side, second measuring tube end into a fourth flow opening $20_{2D}$ of the second flow divider $20_2$. The four measuring tubes $18_1$, $18_2$, $18_3$, $18_4$ are, thus, connected to the flow dividers $20_1$, $20_2$, especially equally constructed flow dividers $20_1$, $20_2$, to form flow paths connected in parallel, and, indeed, in a manner enabling vibrations, especially bending oscillations, of the measuring tubes relative to one another, as well as also relative to the transducer housing. Additionally, it is provided, that the four measuring tubes $18_1$, $18_2$, $18_3$, $18_4$ are held in the transducer housing $7_1$ only by means of said flow dividers $20_1$, $20_2$.

Figure 4:
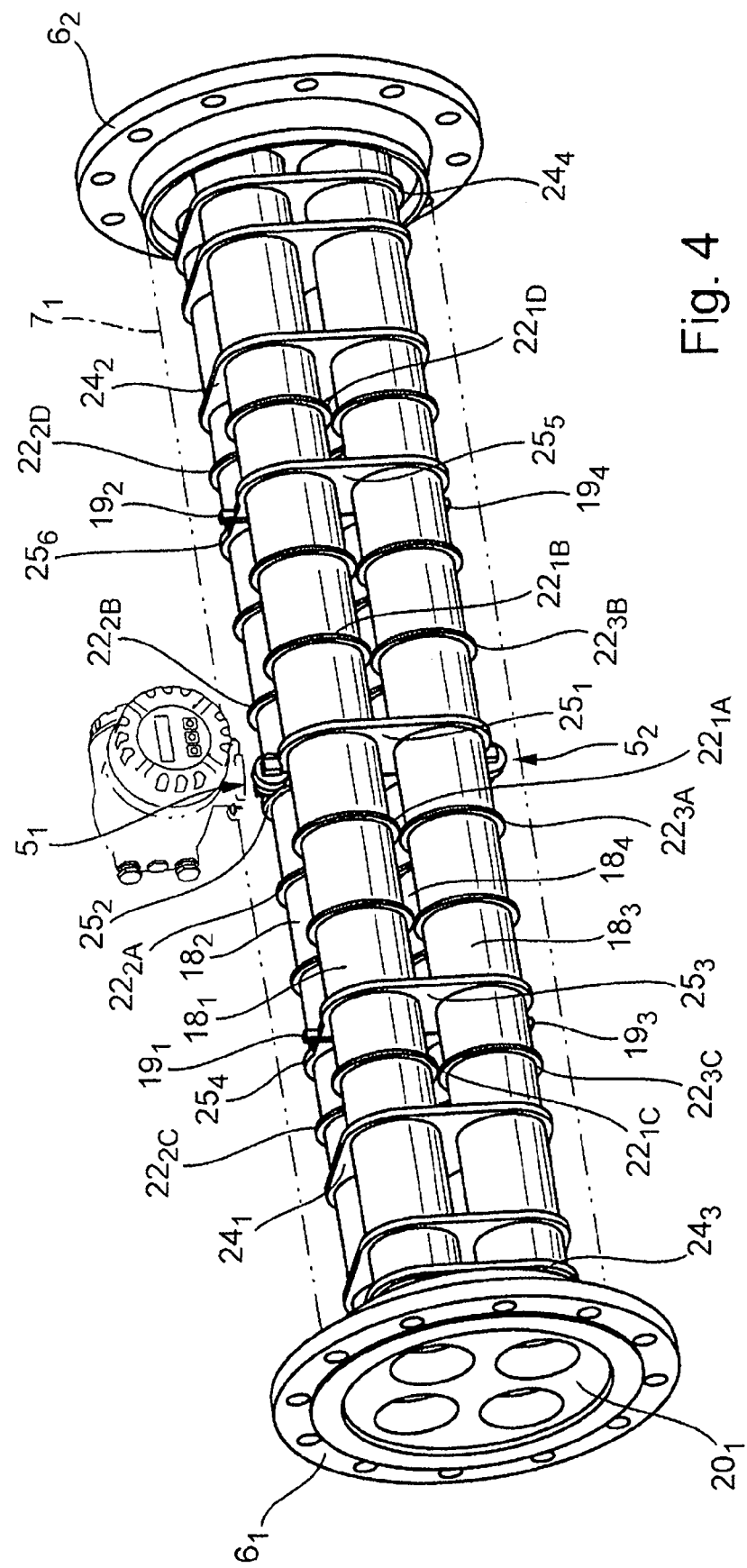
FIG. 4 in perspective, side view, a measuring transducer of vibration-type, installed in an in-line measuring device of FIG. 1.

The measuring tubes $18_1$, $18_2$, $18_3$, $18_4$, or a therewith formed, inner part of the measuring transducer 11, are, such as directly evident from the combination of FIGS. 1, 2 and 4 and such as also usual in the case of such measuring transducers, encased by the transducer housing $7_1$, in the illustrated case practically completely. Transducer housing $7_1$ serves, in this regard, thus not only as support frame or holder of the measuring tubes $18_1$, $18_2$, $18_3$, $18_4$, but also for protecting them, as well as also other components of the measuring transducer placed within the transducer housing $7_1$, from external environmental influences, such as e.g. dust or water spray. Moreover, the transducer housing $7_1$ can additionally also be so embodied and so dimensioned, that it can, in the case of possible damage to one or a plurality of the measuring tubes, e.g. through crack formation or bursting, completely retain outflowing medium up to a required maximum positive pressure in the interior of the transducer housing $7_1$ as long as possible, wherein such critical state can, such as, for example, also indicated in the initially mentioned U.S. Pat. No. 7,392,709, be registered and signaled by means of corresponding pressure sensors and/or on the basis of operating parameters produced internally, during operation, by the mentioned measuring device electronics. Used as material for the transducer housing $7_1$ can be, accordingly, especially, steels, such as, for instance, structural steel, or stainless steel, or also other suitable, or usually suitable for this application, high strength materials.

According to an embodiment of the invention, the four measuring tubes $18_1$, $18_2$, $18_3$, $18_4$ are additionally so embodied and so installed in the measuring transducer 11, that at least the minimum bending oscillation, resonance frequencies $f18_1$, $f18_2$ of the first and second measuring tubes $18_1$, $18_2$ are essentially equal and at least the minimum bending oscillation, resonance frequencies $f18_3$, $f18_4$ of the third and fourth measuring tubes $18_3$, $18_4$ are essentially equal.

According to an additional embodiment of the invention, at least the first and second measuring tubes $18_1$, $18_2$ are of equal construction as regards a material, of which their tube walls are composed, and/or as regards their geometric tube dimensions, especially a tube length, a tube wall thickness, a tube outer diameter and/or a caliber. Additionally, also at least the third and fourth measuring tubes $18_3$, $18_4$ are of equal construction as regards a material, of which their tube walls are composed, and/or as regards their geometric tube dimensions, especially a tube length, a tube wall thickness, a tube outer diameter and/or a caliber, so that, as a result, the four measuring tubes $18_1$, $18_2$, $18_3$, $18_4$ are, at least pairwise, essentially of equal construction. According to an additional embodiment of the invention, it is, in such case, additionally provided, to construct both the third measuring tube as well as also the fourth measuring tube, such that the two measuring tubes are different from the first measuring tube and from the second measuring tube, as regards their respective geometric tube dimensions, especially a tube length, a tube wall thickness, a tube outer diameter and/or a caliber, especially in such a manner, that the minimum bending oscillation, resonance frequencies of the four measuring tubes are only pairwise equal. Through the, thus, created symmetry breaking in the case of the four measuring tubes $18_1$, $18_2$, $18_3$, $18_4$, among other things, the sensitivity, the oscillatory behavior, especially the mechanical eigenfrequencies, and/or the cross sensitivity to the primary, measuring influencing, disturbance variables, such as, for instance, a temperature, or pressure, distribution, the loading of the medium with impurities, etc., of the two, in this respect, mutually different, measuring tube pairs $18_1$, $18_2$, or $18_3$, $18_4$, can be matched, with targeting, to one another and, thus, an improved diagnosis of the measuring transducer, during operation, can be enabled. Of course, the four measuring tubes $18_1$, $18_2$, $18_3$, $18_4$, can, in case required, however, also be of equal construction as regards a material, of which their tube walls are composed, and/or as regards their geometric tube dimensions, especially a tube length, a tube wall thickness, a tube outer diameter and/or a caliber, especially in such a manner, that, as a result, the minimum bending oscillation, resonance frequencies of all four measuring tubes $18_1$, $18_2$, $18_3$, $18_4$ are essentially equal.

Suited as material for the tube walls of the measuring tubes is, again, especially, titanium, zirconium or tantalum. However, serving as material for the four measuring tubes $18_1$, $18_2$, $18_3$, $18_4$ can be also practically any other therefor usually applied, or at least suitable, material, especially such with a thermal expansion coefficient as small as possible and a yield point as high as possible. For most applications of industrial measurements technology, especially also in the petrochemical industry, consequently, also measuring tubes of stainless steel, for example, also duplex steel or super duplex steel, would satisfy the requirements as regards mechanical strength, chemical resistance as well as thermal requirements, so that in numerous cases of application of the transducer housing $7_1$, the flow dividers $20_1$, $20_2$, as well as also the tube walls of the measuring tubes $18_1$, $18_2$, $18_3$, $18_4$ can, in each case, be made of steel of, in each case, sufficiently high quality, this being of advantage, especially as regards material, and manufacturing, costs, as well as also as regards the thermally related dilation behavior of the measuring transducer 11, during operation.

In an additional advantageous embodiment of the invention, the flow openings of the first flow divider $20_1$ are additionally so arranged, that imaginary areal centers of gravity, which belong to the cross sectional areas, here, circularly shaped cross sectional areas, of the flow openings of the first flow divider lying in a shared, imaginary, cutting plane of the first flow divider extending perpendicularly to a longitudinal axis of the measuring transducer, especially a longitudinal axis parallel to a principal flow axis of the measuring transducer, form the vertices of an imaginary square. Additionally, the flow openings of the second flow divider $20_2$ are so arranged, that imaginary areal centers of gravity belonging to the, here, likewise circularly shaped, cross sectional areas of the flow openings of the second flow divider $20_2$ form the vertices of an imaginary square, wherein such cross sectional areas lie, in turn, in a shared, imaginary, cutting plane of the second flow divider extending perpendicularly to a longitudinal axis of the measuring transducer, especially a longitudinal axis parallel to a principal flow axis of the measuring transducer. As a result of this, an envelope the four measuring tubes $18_1$, $18_2$, $18_3$, $18_4$ forms essentially a right cuboid-like body with a square-like base having a quadruple symmetry, whereby the space requirement of the inner part formed by means of the four measuring tubes $18_1$, $18_2$, $18_3$, $18_4$ can be minimized in a manner supporting the compactness of the measuring transducer 11 as a whole.

According to an additional embodiment of the invention, each of the measuring tubes is additionally so arranged in the measuring transducer, that a smallest lateral separation of each of the four measuring tubes (here, of equal length) from a housing side wall of the transducer housing is, in each case, greater than zero, especially, however, greater than 3 mm and/or greater than twice a respective tube wall thickness, or that a smallest lateral separation between two neighboring measuring tubes is, in each case, greater than 3 mm and/or greater than the sum of their respective tube wall thicknesses. Accordingly, additionally, each of the flow openings is so arranged, that a smallest lateral separation of each of the flow openings from a housing side wall of the transducer housing $7_1$ is, in each case, greater than zero, especially greater than 3 mm and/or greater than twice a smallest tube wall thickness of the measuring tubes $18_1$, $18_2$, $18_3$, $18_4$, or that a smallest lateral separation between the flow openings is greater than 3 mm and/or greater than twice a smallest tube wall thickness of the measuring tubes $18_1$, $18_2$, $18_3$, $18_4$. For such purpose, according to an additional embodiment of the invention, the four measuring tubes $18_1$, $18_2$, $18_3$, $18_4$ and the transducer housing $7_1$ are so dimensioned and matched to one another, that a housing to measuring tube, inner diameter ratio of the measuring transducer, as defined by a ratio of the largest housing inner diameter to a caliber at least of the first measuring tube is greater than 3, especially greater than 4 and/or smaller than 5.

As already initially mentioned, in the case of the measuring transducer 11, the reaction forces required for the measuring are effected in the medium being measured by causing the measuring tubes $18_1$, $18_2$, $18_3$, $18_4$ to oscillate in the so-called wanted mode. For such purpose, the measuring transducer comprises additionally an exciter mechanism 5 formed by means of at least one electromechanical, for example, electrodynamic, oscillation exciter acting on the measuring tubes $18_1$, $18_2$, $18_3$, $18_4$, and serving for causing each of the measuring tubes, operationally, at least at times, to execute, and to maintain, oscillations suitable, in each case, for the particular measuring, especially bending oscillations, in the so-called wanted mode, with, in each case, sufficiently large oscillation amplitude for producing and registering the above named reaction forces in the medium. The at least one oscillation exciter serves, in such case, especially for converting an electrical excitation power $P_{exc}$ fed from a corresponding measuring, and operating, circuit e.g. of the above named Coriolis, mass flow meter into such, e.g. pulsating or harmonic, exciter forces Fexc, which act, as simultaneously as possible, uniformly, however, with opposite sense, on the measuring tubes. The exciter forces $F_{exc}$ can be tuned, in manner known, per se, to those skilled in the art, by means provided in the already mentioned measuring, and operating, electronics, e.g. by means of an electrical current, and/or voltage, control circuit, as regards their amplitude, and e.g. by means of phase control loop (PLL), as regards their frequency; compare, for this, for example, also U.S. Pat. No. 4,801,897 or U.S. Pat. No. 6,311,136.

As a result of medium flowing through the measuring tubes excited to oscillations in the wanted mode, there are induced in the medium Coriolis forces, which, in turn, effect deformations of the measuring tubes corresponding to an additional, higher oscillation mode of the measuring tubes, the so-called Coriolis mode. For example, the measuring tubes $18_1$, $18_2$, $18_3$, $18_4$ can, during operation, be excited, by the electromechanical exciter mechanism acting thereon, to bending oscillations, especially to an instantaneous mechanical eigenfrequency of the inner part formed by means of the four measuring tubes $18_1$, $18_2$, $18_3$, $18_4$, in the case of which they are—at least predominantly—laterally deflected in respective planes of oscillation and, such as directly evident from the combination of FIGS. 3a, 3b, or 6a, 6b, are caused to oscillate pairwise in a shared plane of oscillation $XZ_1$, or $XZ_2$, relative to one another with essentially opposite phase. This, in particular, in such a manner, that vibrations executed by each of the measuring tubes $18_1$, $18_2$, $18_3$, $18_4$, during operation, simultaneously, are developed, at least at times, and/or at least partially, in each case, as bending oscillations about an imaginary, measuring tube longitudinal axis connecting the first and the, in each case, associated second measuring tube end of the respective measuring tube, wherein the four measuring tube longitudinal axes extend, in the here illustrated example of an embodiment with four mutually parallel measuring tubes $18_1$, $18_2$, $18_3$, $18_4$ equally parallel relative to one another, such as do the measuring tubes $18_1$, $18_2$, $18_3$, $18_4$, and, moreover, also essentially parallel to an imaginary longitudinal axis of the total measuring transducer imaginarily connecting the two flow dividers and extending through a center of mass of the measuring transducer. In other words, the measuring tubes can, such as quite usual in the case of measuring transducers of vibration-type, in each case, at least sectionally, be caused to oscillate in a bending oscillation mode in the manner of a string clamped on both ends. Accordingly, in an additional embodiment, the first and second measuring tubes $18_1$, $18_2$ are caused, in each case, to execute bending oscillations, which lie in a shared first plane of oscillation $XZ_1$, and, thus, are essentially coplanar. Additionally, it is provided that the third and fourth measuring tubes $18_3$, $18_4$ equally oscillate in a shared, second plane of oscillation $XZ_2$, especially one essentially parallel to the first plane of oscillation $XZ_1$, with opposite phase relative to one another; compare, for this, also FIGS. 6a, 6b.

In an additional embodiment of the invention, the measuring tubes $18_1$, $18_2$, $18_3$, $18_4$ are excited by means of the exciter mechanism 5, during operation, at least partially, especially predominantly, to bending oscillations, which have a bending oscillation frequency, which is about equal to an instantaneous mechanical resonance frequency of the inner part comprising the four measuring tubes $18_1$, $18_2$, $18_3$, $18_4$ or which at least lies in the vicinity of such an eigen-, or resonance, frequency. The instantaneous mechanical bending oscillation resonance frequencies are, in such case, as is known, dependent in special measure on size, shape and material of the measuring tubes $18_1$, $18_2$, $18_3$, $18_4$, as well as also on an instantaneous density of the medium flowing through the measuring tubes, and can, thus, during operation of the measuring transducer, be variable within a wanted frequency band having an expanse of several kilohertz. In the exciting of the measuring tubes to a bending oscillation resonance frequency, on the one hand, an average density of the medium instantaneously flowing through the four measuring tubes can be easily ascertained on the basis of the instantaneously excited oscillation frequency. On the other hand, also, in such manner, the electrical power instantaneously required for maintaining the oscillations excited in the wanted mode can be minimized. Especially, the four measuring tubes $18_1$, $18_2$, $18_3$, $18_4$, driven by the exciter mechanism, additionally, are, at least at times, caused to oscillate with essentially equal oscillation frequency, especially at a shared natural mechanical eigenfrequency of the inner part. Moreover, it is provided that the measuring tubes $18_1$, $18_2$, $18_3$, $18_4$, caused to oscillate at essentially equal frequency, are so excited, that, at least in the case of no flowing medium, the first and third measuring tubes $18_1$, $18_3$ oscillate essentially synchronously relative to one another, i.e. with essentially equal oscillation form, essentially equal phase position and about equal oscillation amplitude. In manner analogous thereto, in the case of this embodiment of the invention, also the second and fourth measuring tubes $18_2$, $18_4$ are caused to oscillate essentially synchronously relative to one another.

The exciter mechanism according to an embodiment of the invention, is embodied in such a manner that, therewith, the first measuring tube $18_1$ and the second measuring tube $18_2$ are excitable, during operation, to opposite phase, bending oscillations in the shared first plane of oscillation $XZ_1$ and the third measuring tube $18_3$ and the fourth measuring tube $18_4$, during operation, to opposite phase bending oscillations in the shared second plane of oscillation $XZ_2$, especially a shared second plane of oscillation $XZ_2$ essentially parallel to the first plane of oscillation $XZ_1$. In an additional embodiment of the invention, the exciter mechanism 5 is formed therefor by means of a first oscillation exciter $5_1$, especially an electrodynamic, first oscillation exciter $5_1$ and/or a first oscillation exciter $5_1$ differentially exciting oscillations of the first measuring tube $18_1$ relative to the second measuring tube $18_2$.

Additionally, it is provided, that the first oscillation exciter $5_1$ is an oscillation exciter of electrodynamic type acting simultaneously, especially differentially, on at least two of the measuring tubes $18_1$, $18_2$, $18_3$, $18_4$. Accordingly, the first oscillation exciter $5_1$ is formed additionally by means of a permanent magnet held on the first measuring tube and a cylindrical coil permeated by the magnetic field of the permanent magnet and held on the second measuring tube, especially in such a manner of a coil, plunging arrangement, in the case of which the cylindrical coil is arranged coaxially to the permanent magnet and the permanent magnet is embodied in the form of an armature moved plungingly within the coil. In a further development of the invention, the exciter mechanism comprises additionally a second oscillation exciter $5_2$, especially an electrodynamic, second oscillation exciter $5_2$ and/or a second oscillation exciter $5_2$ constructed equally to the first oscillation exciter $5_1$ and/or differentially exciting oscillations of the third measuring tube $18_3$ relative to the fourth measuring tube $18_4$. The two oscillation exciters can, in advantageous manner, be interconnected electrically in series, especially in such a manner, that a combined driver signal excites oscillations of the first and third measuring tubes $18_1$, $18_3$ together relative to the second and fourth measuring tubes $18_2$, $18_4$. In an additional embodiment, the second oscillation exciter $5_2$ is formed by means of a permanent magnet held on the third measuring tube and a cylindrical coil permeated by the magnetic field of the permanent magnet and held on the fourth measuring tube.

As shown in FIG. 4, the first oscillation exciter $5_1$ is arranged in above the first and second measuring tubes $18_1$, $18_2$ and, thus, also above a combined local center of gravity of all four measuring tubes $18_1$, $18_2$, $18_3$, $18_4$, which lies in an imaginary cross sectional plane passing through the installed position of said oscillation exciter, whose inner part is formed by means of the four measuring tubes. As a result of the arrangement of at least one oscillation exciter of the exciter mechanism 5 outside of the above described combined center of gravity of the four measuring tubes, supplementally to bending oscillations, in advantageous manner, also wanted torsional oscillations can be excited, simultaneously or intermittently. In this way, in medium instantaneously located in the measuring tubes $18_1$, $18_2$, $18_3$, and $18_4$, respectively, in considerable measure, also frictional, or shear, forces, principally dependent on viscosity, can be induced, which, in turn, react dampingly and, thus, measurably, on the oscillations of the measuring tubes $18_1$, $18_2$, $18_3$, and $18_4$, respectively. Based thereon, for example, on the basis of the driver signal fed into the exciter mechanism 5, especially its electrical current level, in case required, also a viscosity of the medium guided in the measuring transducer can be ascertained.

It is noted here, additionally, that, although the oscillation exciter of the exciter mechanism illustrated in the example of an embodiment acts, in each case, about centrally on the measuring tubes, alternatively or in supplementation also oscillation exciters acting on the inlet and on the outlet sides on the respective measuring tubes can be used, for instance in the manner of the exciter mechanisms proposed in U.S. Pat. No. 4,823,614, U.S. Pat. No. 4,831,885, or US-A 2003/0070495.

As evident from FIGS. 2 and 4 and usual in the case of measuring transducers of the type being discussed, additionally provided in the measuring transducer 11 is a sensor arrangement 19, for example, an electrodynamic sensor arrangement, reacting to vibrations of the measuring tubes $18_1$, $18_2$, $18_3$, or $18_4$, especially inlet, and outlet-side vibrations, especially bending oscillations excited by means of the exciter mechanism 5, for producing oscillation measurement signals representing vibrations, especially bending oscillations, of the measuring tubes and influenced, for example, as regards a frequency, a signal amplitude and/or a phase position—relative to one another and/or relative to the driver signal—by the measured variable to be registered, such as, for instance, the mass flow rate and/or the density and a viscosity of the medium, respectively.

In an additional embodiment of the invention, the sensor arrangement is formed by means of an inlet-side, first oscillation sensor $19_1$, especially an electrodynamic, first oscillation sensor and/or a first oscillation sensor differentially registering at least oscillations of the first measuring tube $18_1$ relative to the second measuring tube $18_2$, as well as an outlet-side, second oscillation sensor $19_2$, especially an electrodynamic, second oscillation sensor and/or a second oscillation sensor differentially registering at least oscillations of the first measuring tube $18_1$ relative to the second measuring tube $18_2$, which two oscillation sensors deliver, respectively, a first, and a second, oscillation measurement signal reacting to movements of the measuring tubes $18_1$, $18_2$, $18_3$, $18_4$, especially their lateral deflections and/or deformations. This, especially, in such a manner, that at least two of the oscillation measurement signals delivered by the sensor arrangement 19 have a phase shift relative to one another, which corresponds to, or depends on, the instantaneous mass flow rate of the medium flowing through the measuring tubes, as well as, in each case, a signal frequency, which depends on an instantaneous density of the medium flowing in the measuring tubes. The two oscillation sensors $19_1$, $19_2$, for example, oscillation sensors constructed equally to one another, can, for such purpose—such as quite usual in the case of measuring transducers of the type being discussed—be placed essentially equidistantly from the first oscillation exciter $5_1$ in the measuring transducer 11. Moreover, the oscillation sensors of the sensor arrangement 19 can, at least, insofar as they are of equal construction to that of the at least one oscillation exciter of the exciter mechanism 5, work analogously to its principle of action, for example, thus be likewise of electrodynamic type. In a further development of the invention, the sensor arrangement 19 is additionally formed also by means of an inlet-side, third oscillation sensor $19_3$, especially an electrodynamic, oscillation sensor and/or an oscillation sensor differentially registering oscillations of the third measuring tube $18_3$ relative to the fourth measuring tube $18_4$, as well as an outlet-side, fourth oscillation sensor $19_4$, especially an electrodynamic, fourth oscillation sensor $19_4$ and/or an electrodynamic oscillation sensor differentially registering oscillations of the third measuring tube $18_3$ relative to the fourth measuring tube $18_4$. For additional improving of the signal quality, as well as also for simplifying the measuring device electronics 12 receiving the measurement signals, furthermore, the first and third oscillation sensors $19_1$, $19_3$ can be electrically in series interconnected, for example, in such a manner, that a combined oscillation measurement signal represents combined inlet-side oscillations of the first and third measuring tubes $18_1$, $18_3$ relative to the second and fourth measuring tubes $18_2$, $18_4$. Alternatively or in supplementation, also the second and fourth oscillation sensors $19_2$, $19_4$ can be electrically in series interconnected in such a manner, that a combined oscillation measurement signal of both oscillation sensors $19_2$, $19_4$ represents combined outlet-side oscillations of the first and third measuring tubes $18_1$, $18_3$ relative to the second and fourth measuring tubes $18_2$, $18_4$.

For the aforementioned case, that the oscillation sensors of the sensor arrangement 19, especially oscillation sensors constructed equally to one another, should register oscillations of the measuring tubes differentially and electrodynamically, the first oscillation sensor $19_1$ is formed by means of a permanent magnet held to the first measuring tube—here in the region of oscillations to be registered on the inlet side—and a cylindrical coil permeated by the magnetic field of the permanent magnet and held to the second measuring tube—here correspondingly likewise in the region of oscillations to be registered on the inlet side—, and the second oscillation sensor $19_2$ is formed by means of a permanent magnet held—in the region of oscillations to be registered on the outlet side—to the first measuring tube and a cylindrical coil permeated by the magnetic field of the permanent magnet and held to the second measuring tube—here correspondingly likewise in the region of oscillations to be registered on the outlet side. Equally, additionally also the, in given cases, provided, third oscillation sensor $19_3$ can correspondingly be formed by means of a permanent magnet held to the third measuring tube and a cylindrical coil permeated by the magnetic field of the permanent magnet and held to the fourth measuring tube, and the, in given cases, provided, fourth oscillation sensor $19_4$ by means of a permanent magnet held to the third measuring tube and a cylindrical coil permeated by the magnetic field of the permanent magnet and held to the fourth measuring tube.

It is to be noted here additionally that, although, in the case of the oscillation sensors of the sensor arrangement 19 illustrated in the example of an embodiment, the oscillation sensor is, in each case, of electrodynamic type, thus, in each case, formed by means of a cylindrical magnet coil affixed to one of the measuring tubes and a therein plunging permanent magnet correspondingly affixed to an oppositely lying measuring tube, additionally also other oscillation sensors known to those skilled in the art, such as e.g. optoelectronic sensors, can be used for forming the sensor arrangement. Furthermore, such as quite usual in the case of measuring transducers of the type being discussed, supplementally to the oscillation sensors, other, especially auxiliary sensors, or sensors registering disturbance variables, can be provided in the measuring transducer, such as e.g. acceleration sensors, pressure sensors and/or temperature sensors, by means of which, for example, the ability of the measuring transducer to function and/or changes of the sensitivity of the measuring transducer to the measured variables primarily to be registered, especially the mass flow rate and/or the density, as a result of cross sensitivities, or external disturbances, can be monitored and, in given cases, correspondingly compensated.

For assuring an as high as possible sensitivity of the measuring transducer to the mass flow, according to an additional embodiment of the invention, the oscillation sensors are so arranged on the measuring tubes in the measuring transducer, that a measuring length, $L_{19}$, of the measuring transducer corresponding to a minimum separation between the first oscillation sensor $19_1$ and the second oscillation sensor $19_2$, amounts to more than 500 mm, especially more than 600 mm.

The exciter mechanism 5 and the sensor arrangement 19 are additionally, such as usual in the case of such measuring transducers, coupled in suitable manner (for example, hardwired by means of corresponding cable connections) with a measuring, and operating, circuit correspondingly provided in the measuring device electronics. The measuring, and operating, circuit, in turn, produces, on the one hand, an exciter signal correspondingly driving the exciter mechanism 5, for example, an exciter signal controlled as regards an exciter current and/or an exciter voltage. On the other hand, the measuring, and operating, circuit receives the oscillation measurement signals of the sensor arrangement 19 and generates, therefrom, sought measured values, which, for example, can represent a mass flow rate, a totaled mass flow, a density and/or a viscosity of the medium being measured and which, in given cases, can be displayed on-site and/or also sent to a data processing system superordinated to the in-line measuring device, in the form of digital, measured data and there correspondingly further processed. The above mentioned application of differentially acting, oscillation exciters, or oscillation sensors, in the case of the here illustrated inner part, introduces, among other things, also the advantage, that for operating the measuring transducer of the invention, also such established measuring, and operating, electronics can be used, such as have found broad application, for example, already in conventional Coriolis, mass flow and/or density measuring devices.

The measuring device electronics 12, including the measuring, and operating, circuit, can, furthermore, be accommodated, for example, in a separate electronics housing $7_2$, which is arranged removed from the measuring transducer or, such as shown in FIG. 1, is affixed directly on the measuring transducer 1, for example, externally on the transducer housing $7_1$, in order to form a single compact device. In the case of the here illustrated example of an embodiment, consequently, placed on the transducer housing $7_1$ is, additionally, a neck-like, transition piece serving for holding the electronics housing $7_2$. Within the transition piece can additionally be arranged a feedthrough for the electrical connecting lines between measuring transducer 11, especially the therein placed oscillation exciters and sensors, and the mentioned measuring device electronics 12. The feedthrough is manufactured to be hermetically sealed and/or pressure resistant, for example, by means of glass, and/or plastic potting compound.

As already multiply mentioned, the in-line measuring device and, thus, also the measuring transducer 11, is provided, especially, for measurements also of high mass flows of more than 2200 t/h in a pipeline of large caliber of more than 250 mm. Taking this into consideration, according to an additional embodiment of the invention, the nominal diameter of the measuring transducer 11, which, as already mentioned, corresponds to a caliber of the pipeline, in whose course the measuring transducer 11 is to be used, is so selected, that it amounts to more than 100 mm, especially, however, is greater than 300 mm. Additionally, according to a further embodiment of the measuring transducer, it is provided, that each of the measuring tubes $18_1$, $18_2$, $18_3$, $18_4$ has, in each case, a caliber $D_{18}$ corresponding to a particular tube inner diameter, which amounts to more than 60 mm. Especially, the measuring tubes $18_1$, $18_2$, $18_3$, $18_4$ are additionally so embodied, that each has a caliber $D_{18}$ of more than 80 mm. Alternatively thereto or in supplementation thereof, the measuring tubes $18_1$, $18_2$, $18_3$, $18_4$ are, according to another embodiment of the invention, additionally so dimensioned, that they have, in each case, a measuring tube length $L_{18}$ of at least 1000 mm. The measuring tube length $L_{18}$ corresponds, in the here illustrated example of an embodiment with equal length measuring tubes $18_1$, $18_2$, $18_3$, $18_4$, in each case, to a minimum separation between the first flow opening $20_{1A}$ of the first flow divider $20_1$ and the first flow opening $20_{2A}$ of the second flow divider $20_2$. Especially, the measuring tubes $18_1$, $18_2$, $18_3$, $18_4$ are, in such case, so designed, that their measuring tube length $L_{18}$ is, in each case, greater than 1200 mm.

Accordingly, there results, at least for the mentioned case, that the measuring tubes $18_1$, $18_2$, $18_3$, $18_4$ are composed of steel, in the case of the usually used wall thicknesses of over 1 mm, a mass of, in each case, at least 20 kg, especially more than 30 kg. One tries, however, to keep the empty mass of each of the measuring tubes $18_1$, $18_2$, $18_3$, $18_4$ smaller than 50 kg.

In consideration of the fact that, as already mentioned, each of the measuring tubes $18_1$, $18_2$, $18_3$, $18_4$, in the case of the measuring transducer of the invention, weighs well over 20 kg and, in such case, such as directly evident from the above dimensional specifications, can have a capacity of easily 10 l or more, the inner part comprising then the four measuring tubes $18_1$, $18_2$, $18_3$, $18_4$ can, at least in the case of medium with high density flowing through, reach a total mass of far over 80 kg. Especially in the case of the application of measuring tubes with comparatively large caliber $D_{18}$, large wall thickness and large measuring tube length $L_{18}$, the mass of the inner part formed by the measuring tubes $18_1$, $18_2$, $18_3$, $18_4$ can directly, however, also be greater than 100 kg or, at least with medium flowing through, e.g. oil or water, be more than 120 kg. As a result of this, an empty mass $M_{11}$ of the measuring transducer amounts, in total, also to far more than 200 kg, and, in the case of nominal diameters $D_{11}$ of significantly greater than 250 mm, even more than 300 kg. As a result, the measuring transducer of the invention can have a mass ratio $M_{11}/M_{18}$ of an empty mass $M_{11}$ of the total measuring transducer to an empty mass $M_{18}$ of the first measuring tube of easily greater than 10, especially greater than 15.

In order, in the case of the mentioned high empty mass $M_{11}$ of the measuring transducer, to employ the therefor, in total, applied material as optimally as possible and, thus, to utilize the—most often also very expensive—material, in total, as efficiently as possible, according to an additional embodiment, the nominal diameter $D_{11}$ of the measuring transducer is so dimensioned relative to its empty mass $M_{11}$, that a mass to nominal diameter ratio $M_{11}/D_{11}$ of the measuring transducer 11, as defined by a ratio of the empty mass $M_{11}$ of the measuring transducer 11 to the nominal diameter $D_{11}$ of the measuring transducer 11, is smaller than 2 kg/mm, especially as much as possible, however, smaller than 1 kg/mm. In order to assure a sufficiently high stability of the measuring transducer 11, the mass to nominal diameter ratio $M_{11}/D_{11}$ of the measuring transducer 11 is, at least in the case use of the above mentioned conventional materials, however, to be chosen as much as possible greater than 0.5 kg/mm. Additionally, according to an additional embodiment of the invention, for additional improvement of the efficiency of the installed material, the mentioned mass ratio $M_{11}/M_{18}$ is kept smaller than 25.

For creation of a nevertheless as compact as possible measuring transducer of sufficiently high oscillation quality factor and as little pressure drop as possible, according to an additional embodiment of the invention, the measuring tubes are so dimensioned relative to the above mentioned, installed length $L_{11}$ of the measuring transducer 11, that a caliber to installed length ratio $D_{18}/L_{11}$ of the measuring transducer, as defined by a ratio of the caliber $D_{18}$ at least of the first measuring tube to the installed length $L_{11}$ of the measuring transducer 11, amounts to more than 0.02, especially more than 0.05 and/or less than 0.09. Alternatively or in supplementation, the measuring tubes $18_1$, $18_2$, $18_3$, $18_4$ are so dimensioned relative to the above mentioned installed length $L_{11}$ of the measuring transducer, that a measuring tube length to installed length ratio $L_{18}/L_{11}$ of the measuring transducer, as defined by a ratio of the measuring tube length $L_{18}$ at least of the first measuring tube to the installed length $L_{11}$ of the measuring transducer, amounts to more than 0.7, especially more than 0.8 and/or less than 0.95.

In case required, possibly or at least potentially, mechanical stresses and/or vibrations caused by the vibrating, especially in the mentioned manner, relatively large dimensioned, measuring tubes at the inlet side or at the outlet side in the transducer housing can e.g. be minimized by connecting the four measuring tubes $18_1$, $18_2$, $18_3$, $18_4$ with one another mechanically at least pairwise on the inlet side, and at least pairwise on the outlet side, in each case, by means of coupling elements serving as so-called node plates—in the following referred to as coupling elements of first type. Moreover, by means of such coupling elements of first type, be it through their dimensioning and/or their positioning on the measuring tubes, mechanical eigenfrequencies of the measuring tubes and, thus, also mechanical eigenfrequencies of the inner part formed by means of the four measuring tubes as well as thereon placed, additional components of the measuring transducer and, thus, also its oscillatory behavior, in total, can, with targeting, be influenced.

The coupling elements of first type serving as node plates can, for example, be thin plates, or washers, manufactured especially from the same material as the measuring tubes, which, in each case, corresponding with the number and the outer dimensions of the measuring tubes to be coupled with one another, are provided with bores, in given cases, supplementally, slitted to the edge, so that the washers can first be mounted onto the respective measuring tubes $18_1$, $18_2$, $18_3$, or $18_4$ and, in given cases, thereafter still be bonded to the respective measuring tubes, for example, by hard soldering or welding.

Accordingly, the measuring transducer comprises, according to an additional embodiment of the invention, a first coupling element $24_1$ of first type, which is affixed on the inlet side at least to the first measuring tube and to the second measuring tube and spaced both from the first flow divider as well as also from the second flow divider for forming inlet-side, oscillation nodes at least for vibrations, especially bending oscillations, of the first measuring tube and for thereto opposite phase vibrations, especially bending oscillations, of the second measuring tube, as well as a second coupling element $24_2$ of first type, especially a second coupling element $24_2$ constructed equally to the first coupling element, which is affixed on the outlet side at least to the first measuring tube $18_1$ and to the second measuring tube $18_2$ and spaced both from the first flow divider $20_1$ as well as also from the second flow divider $20_2$, as well as also from the first coupling element $24_1$, for forming outlet-side, oscillation nodes at least for vibrations, especially bending oscillations, of the first measuring tube $18_1$ and for thereto opposite phase vibrations, especially bending oscillations, of the second measuring tube $18_2$. As directly evident from FIG. 4, or FIGS. 5a, 5b, the first coupling element $24_1$ of first type is affixed on the inlet side also to the third measuring tube $18_3$ and to the fourth measuring tube $18_4$ and spaced both from the first flow divider $20_1$ as well as also from the second flow divider $20_2$, for forming inlet-side, oscillation nodes also for vibrations, especially bending oscillations, of the third measuring tube $18_3$ and for thereto opposite phase vibrations, especially bending oscillations, of the fourth measuring tube $18_4$, and the second coupling element $24_2$ of first type is affixed on the outlet side also to the third measuring tube $18_3$ and to the fourth measuring tube $18_4$ and spaced both from the first flow divider $20_1$ as well as also from the second flow divider $20_2$, as well as also from the first coupling element $24_1$, for forming outlet-side, oscillation nodes at least for vibrations, especially bending oscillations, of the third measuring tube $18_3$ and for thereto opposite phase vibrations, especially bending oscillations, of the fourth measuring tube $18_4$, so that, as a result, all four measuring tubes $18_1$, $18_2$, $18_3$, $18_4$ are mechanically connected with one another by means of the first coupling element $24_1$ of first type as well as by means of the second coupling element $24_2$ of first type. Each of the two aforementioned coupling elements $24_1$, $24_2$ of first type, especially coupling elements constructed equally to one another, is, according to an additional embodiment of the invention, plate shaped, especially in such a manner, that it has, as well as also directly evident from the combination of figures, a rather rectangular or also square, basic shape or, however, that it has, rather, a round, an oval, a cross shaped or, such as, for example, also provided in US-A 2006/028326$_4$, a rather H-shaped basic shape. Additionally, the two coupling elements $24_1$, $24_2$ are oriented essentially parallel relative to one another.

Figure 5A:
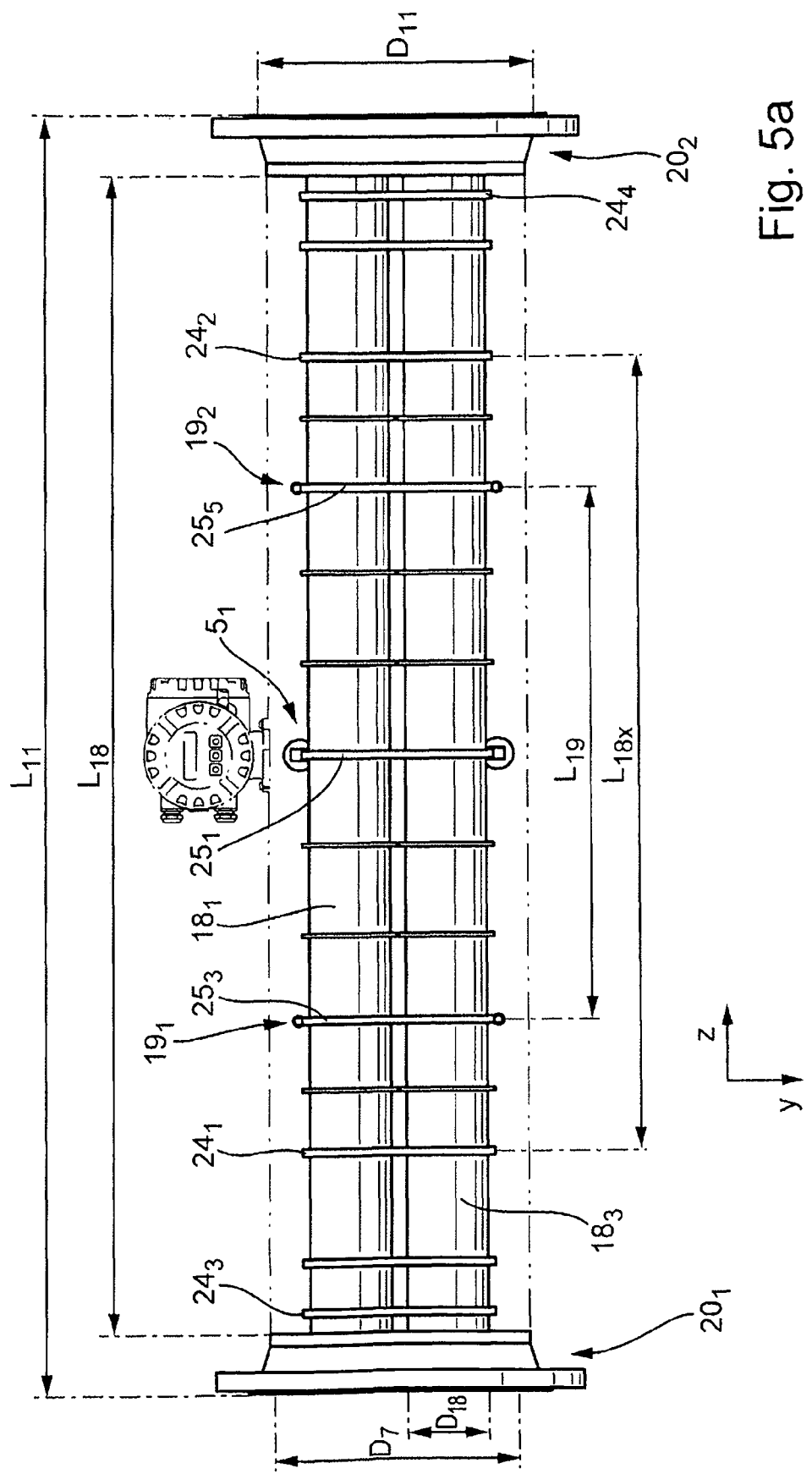
FIGS. 5a, and 5b a projection of the measuring transducer of FIG. 4 in two different side views.
Figure 5B:
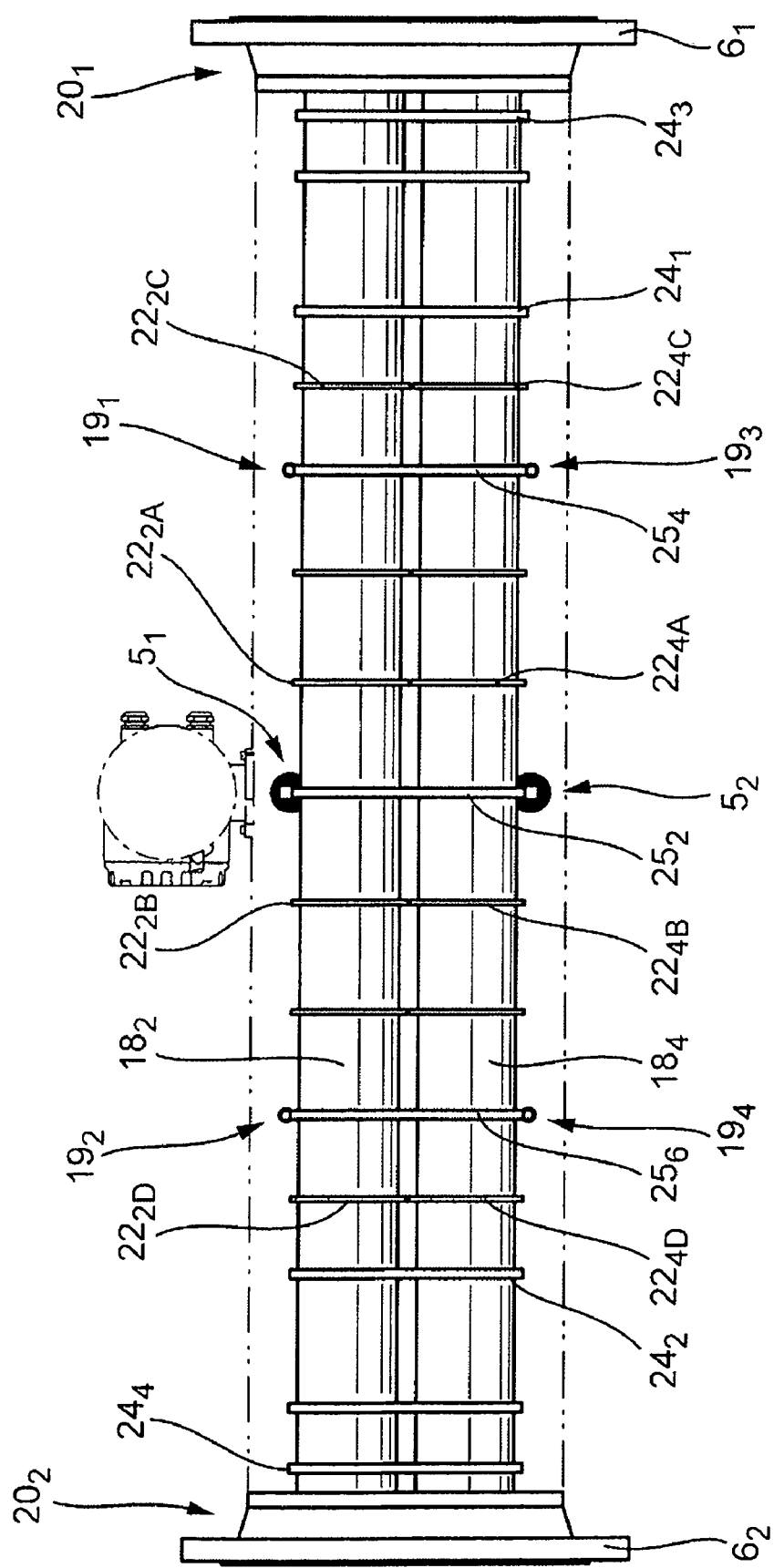

As directly evident from FIG. 4, or FIGS. 5a, 5b, the two aforementioned coupling elements $24_1$, $24_2$ are additionally so embodied and so placed in the measuring transducer, that a center of mass of the first coupling element $24_1$ of first type has a distance to a center of mass of the measuring transducer 11, which is essentially equal to a distance of a center of mass of the second coupling element $24_2$ of first type to said center of mass of the measuring transducer 11, especially in such a manner, that the two coupling elements $24_1$, $24_2$ are, as a result, arranged symmetrically to a shared imaginary cross sectional plane, in each case, cutting centrally through the measuring tubes $18_1$, $18_2$, $18_3$, $18_4$.

For additionally increasing the degrees of freedom in the case of optimizing the oscillatory behavior of the inner part formed by means of the four measuring tubes $18_1$, $18_2$, $18_3$, $18_4$, the measuring transducer 11 comprises, according to a further development of the invention, additionally a third coupling element $24_3$ of first type, which is affixed on the inlet side at least to the third measuring tube $18_3$ and to the fourth measuring tube $18_4$ and spaced both from the first flow divider $20_1$ as well as also from the second flow divider $20_2$ for forming inlet-side, oscillation nodes at least for vibrations, especially bending oscillations, of the third measuring tube $18_3$ and for thereto opposite phase vibrations, especially bending oscillations, of the fourth measuring tube $18_4$. Moreover, the measuring transducer 11 comprises, in the case of this further development, a fourth coupling element $24_4$ of first type, especially a fourth coupling element constructed equally to the third coupling element $24_3$ of first type, which fourth coupling element is affixed on the outlet side at least to the third measuring tube $18_3$ and to the fourth measuring tube $18_4$ and spaced both from the first flow divider $20_1$ as well as also from the second flow divider $20_2$, as well as also from the third coupling element $24_3$ of first type, for forming outlet-side, oscillation nodes at least for vibrations, especially bending oscillations, of the third measuring tube $18_3$ and for thereto opposite phase vibrations, especially bending oscillations, of the fourth measuring tube $18_4$.

Each of the two aforementioned third and fourth coupling elements $24_3$, $24_4$ of first type, especially third and fourth coupling elements constructed equally to one another, is embodied, according to an additional embodiment of the invention, again, plate shaped, especially in such a manner, that it has a rectangular, square, round, cross shaped or H-shaped, basic shape. Additionally, the two aforementioned third and fourth coupling elements $24_3$, $24_4$ are oriented extending essentially parallel relative to one another.

As shown in FIG. 4, or in FIGS. 5a, 5b, the third coupling element $24_3$ of first type is affixed on the inlet side also to the first measuring tube $18_1$ and to the second measuring tube $18_2$ and spaced both from the first flow divider $20_1$ as well also from the second flow divider $20_2$, as well as also from the first coupling element of first type $24_1$ and the fourth coupling element $24_4$ of first type is affixed on the outlet side also to the first measuring tube and to the second measuring tube and spaced both from the first flow divider as well as also from the second flow divider, as well as also from the second coupling element, so that, as a result, all four measuring tubes $18_1$, $18_2$, $18_3$, $18_4$ are also mechanically connected with one another by means of the third coupling element $24_3$ of first type as well as by means of the fourth coupling element $24_4$ of first type.

As directly evident from the combination of FIGS. 4, 5a, 5b, also the third and fourth coupling elements $24_3$, $24_4$ are additionally so embodied and so placed in the measuring transducer, that a center of mass of the third coupling element $24_3$ of first type has a distance to the center of mass of the measuring transducer, which essentially is equal to a distance of a center of mass of the fourth coupling element $24_4$ of first type to said center of mass of the measuring transducer, especially in such a manner, that the two coupling elements $24_3$, $24_4$ are, as a result, arranged symmetrically to a shared imaginary cross sectional plane, in each case, cutting centrally through the four measuring tubes $18_1$, $18_2$, $18_3$, $18_4$. Additionally, according to a further embodiment of the invention, the four coupling element $24_1$, $24_2$, $24_3$, $24_4$ of first type are so arranged in the measuring transducer, that the distance of the center of mass of the third coupling element $24_3$ of first type from the center of mass of the measuring transducer is greater than the distance of the center of mass of the first coupling element $24_1$ of first type from said center of mass of the measuring transducer and greater than the distance of the center of mass of the second coupling element $24_2$ of first type from said center of mass of the measuring transducer.

As directly evident from the combination of FIGS. 4, 5a and 5b, a minimum separation between the coupling element of first type affixed on the inlet side to a particular measuring tube and lying nearest to the center of mass of the measuring transducer 11—here thus the first coupling element $24_1$ of first type—, and the coupling element of first type affixed on the outlet side to said measuring tube and lying nearest to the center of mass of the measuring transducer—here thus the second coupling element $24_2$ of first type—, defines, in each case, a free, oscillatory length, $L_{18x}$, of such measuring tube, wherein, according to an additional embodiment of the invention; the coupling elements of first type are so placed in the measuring transducer, that, as a result, the free, oscillatory length of each of the measuring tubes $18_1$, $18_2$, $18_3$, $18_4$ amounts to less than 2500 mm, especially less than 2000 mm and/or more than 800 mm. Alternatively or in supplementation, it is additionally provided, that all four measuring tubes $18_1$, $18_2$, $18_3$, $18_4$ have the same, free, oscillatory length $L_{18x}$.

It can additionally, in the context of a still simpler and yet more exact adjusting of the oscillatory behavior of the measuring transducer, be quite of advantage, when the measuring transducer, such as, for example, provided in US-A 2006/0150750, moreover, has still other coupling elements of the aforementioned type serving for forming inlet, or outlet, side, oscillation nodes for vibrations, especially bending oscillations, of the first measuring tube and for thereto opposite phase vibrations, especially bending oscillations, of the second measuring tube, or for vibrations, especially bending oscillations, of the third measuring tube and for thereto opposite phase vibrations, especially bending oscillations, of the fourth measuring tube, for example, thus, in total, 6 or 8 such coupling elements of first type.

For creation of an as compact as possible measuring transducer of sufficiently high oscillation quality factor and high sensitivity in the case of as little pressure drop as possible, according to an additional embodiment of the invention, the measuring tubes $18_1$, $18_2$, $18_3$, $18_4$ are so dimensioned relative to the mentioned free, oscillatory length that a caliber to oscillatory length ratio $D_{18}/L_{18x}$ of the measuring transducer, as defined by a ratio of the caliber $D_{18}$ of the first measuring tube to the free, oscillatory length $L_{18x}$ of the first measuring tube, amounts to more than 0.07, especially more than 0.09 and/or less than 0.15. Alternatively or in supplementation, for this, according to an additional embodiment of the invention, the measuring tubes $18_1$, $18_2$, $18_3$, $18_4$ are so dimensioned relative to the above mentioned installed length $L_{11}$ of the measuring transducer that an oscillatory length to installed length ratio $L_{18x}/L_{11}$ of the measuring transducer, as defined by a ratio of the free, oscillatory length $L_{18x}$ of the first measuring tube to the installed length $L_{11}$ of the measuring transducer, amounts to more than 0.55, especially more than 0.6 and/or less than 0.9.

According to an additional embodiment of the invention, the oscillation sensors, relative to the free, oscillatory length, are so arranged in the measuring transducer, that a measuring length to oscillatory length ratio of the measuring transducer, as defined by a ratio of the mentioned measuring length of the measuring transducer to the free, oscillatory length of the first measuring tube, amounts to more than 0.6, especially more than 0.65 and/or less than 0.95.

For creation of an as compact as possible measuring transducer, which is, nevertheless, however, as sensitive as possible to mass flow, according to an additional embodiment of the invention, the oscillation sensors are so arranged in the measuring transducer relative to the installed length of the measuring transducer that a measuring length to installed length ratio of the measuring transducer, which is defined by a ratio of the measuring length to the installed length of the measuring transducer, amounts to more than 0.3, especially more than 0.4 and/or less than 0.7. Alternatively or in supplementation, the oscillation sensors are, according to an additional embodiment of the invention, so placed in the measuring transducer relative to the measuring tubes, that a caliber to measuring length ratio $D_{18}/L_{19}$ of the measuring transducer, which is defined by a ratio of the caliber $D_{18}$ of the first measuring tube to the measuring length $L_{19}$ of the measuring transducer, amounts to more than 0.05, especially more than 0.09. In an additional embodiment of the invention, additionally, the above mentioned measuring length $L_{19}$ is kept smaller than 1200 mm.

In an additional embodiment of the invention, it is further provided that the measuring tubes $18_1$, $18_2$, $18_3$, $18_4$ are driven, during operation, pairwise synchronously, thus with equal phase position, so that the oscillations of all four measuring tubes $18_1$, $18_2$, $18_3$, $18_4$ are only pairwise out of phase. In advantageous manner, the oscillatory behavior of the inner part formed by means of the four measuring tubes $18_1$, $18_2$, $18_3$, $18_4$, together with the exciter mechanism, and the sensor arrangement, as well as also the driver signals controlling the exciter mechanism, are so matched to one another, that at least the oscillations of the four measuring tubes $18_1$, $18_2$, $18_3$, $18_4$ excited in the wanted mode are so developed, that the first and the second measuring tubes $18_1$, $18_2$ oscillate with essentially opposite phase relative to one another, thus with an opposing phase shift of about 180°, and also the third and fourth measuring tubes $18_3$, $18_4$ oscillate with essentially opposite phase relative to one another, while, simultaneously, the first and third measuring tubes $18_1$, $18_3$ oscillate with essentially equal phase relative to one another and the second and fourth measuring tubes $18_2$, $18_4$ oscillate with essentially equal phase relative to one another.

Therefore, the measuring transducer includes, according to a further embodiment of the invention, additionally a first coupling element $25_1$ of second type, especially a plate shaped or rod shaped, first coupling element $25_1$ of second type, which is affixed to the first measuring tube $18_1$ and to the third measuring tube $18_3$, but, otherwise, to no other measuring tube, thus only to the first measuring tube $18_1$ and to the third measuring tube $18_3$, and spaced both from the first coupling element $24_1$ of first type as well as also from the second coupling element $24_2$ of first type, for synchronizing vibrations, especially bending oscillations, of the first measuring tube $18_1$ and thereto equal frequency vibrations, especially bending oscillations, of the third measuring tube $18_3$. Furthermore, the measuring transducer comprises, at least in the case of this embodiment of the invention, at least a second coupling element $25_2$ of second type, especially a plate shaped or rod shaped, second coupling element $25_2$ of second type, which is affixed to the second measuring tube $18_2$ and to the fourth measuring tube $18_4$, but otherwise to no other measuring tube, thus only to the second measuring tube $18_2$ and to the fourth measuring tube $18_4$, and spaced both from the first coupling element $24_1$ of first type as well as also from the second coupling element $24_1$ of first type, as well as also from the first coupling element $25_1$ of second type, for synchronizing vibrations, especially bending oscillations, of the second measuring tube $18_2$ and thereto equal frequency vibrations, especially bending oscillations, of the fourth measuring tube $18_4$. As directly evident from the combination of FIGS. 4, 5a and 5b, the first and second coupling elements $25_1$, $25_2$ of second type are placed in the measuring transducer 11 as oppositely lying to one another as possible.

An advantage of the mechanical coupling of the measuring tubes in the above described manner is, among other things, to be seen in the fact that the four measuring tubes $18_1$, $18_2$, $18_3$, $18_4$ are reduced to two measuring tube composites acting, in each case, effectively as one oscillatory system, each thus acting essentially as a single measuring tube, since the exciter forces produced by the exciter mechanism 5 act, due to the mechanical coupling, both between the first and second measuring tubes $18_1$, $18_2$ as well as also equally between the third and fourth measuring tubes $18_3$, $18_4$, and, in turn, also the reaction forces caused in the through-flowing media for purposes of the measuring are transmitted, in each case, together back to the oscillation sensors of the sensor arrangement 5. Furthermore, possible differences between the individual measuring tubes $18_1$, $18_2$, $18_3$, $18_4$ can as regards their nominal oscillatory behavior, e.g. as a result of non-uniform flow, different temperatures, and/or different density distributions, etc., be cancelled in very simple manner. The application of coupling elements of second type has additionally also the advantage, that each of the two measuring tube composites formed, thus, in very simple manner, acts, not only for the exciter mechanism, but equally also for the sensor arrangement 19, and, thus, also for the measuring, and operating, circuit of the measuring device electronics 12, in total, practically, in each case, as a single measuring tube, and the measuring transducer 11, thus, from the point of view of the measuring, and operating, circuit, seems to have only two measuring tubes oscillating relative to one another. As a result of this, at least for the preprocessing and possible digitizing of the oscillation measurement signals, proven signal processing technologies and also proven, especially two channel (thus processing oscillation measurement signals delivered from only two oscillation sensors) measuring circuits from the field of Coriolis, mass flow, or density measurement, can be utilized. Equally, thus, also for the operating circuit driving the exciter mechanism, driver circuits known to those skilled in the art, especially such operating on one channel, thus delivering exactly one driver signal for the exciter mechanism, can be directly used. In case required, however, also the oscillation measurement signals delivered, in each case, from the two or more oscillation sensors can, however, also be individually preprocessed and correspondingly digitized in, in each case, separate measuring channels; equally, in case required, also the, in given cases, present, two or more oscillation exciters can be operated separately by means of separate driver signals.

According to an embodiment of the invention, the measuring tubes $18_1$, $18_2$, $18_3$, $18_4$, as well as the coupling elements connecting these with one another, are, consequently, additionally so formed and so mechanically coupled with one another by means of coupling elements of second type, in given cases, supplementally also by means of coupling elements of first type, that a first measuring tube composite formed from the first and the third measuring tubes $18_1$, $18_3$ and a second measuring tube composite formed by the second and the fourth measuring tubes $18_2$, $18_4$ have essentially the same mechanical eigenfrequencies.

In the example of an embodiment shown here, the first coupling element $25_1$ of second type is affixed to the first and third, measuring tubes $18_1$, $18_3$, respectively, in the region of 50% of a minimum separation between the first coupling element $24_1$ of first type and the second coupling element $24_2$ of first type—, as a result, thus at about half the free, oscillatory length of the first and third Measuring tubes $18_1$, $18_3$, respectively. Additionally, also the second coupling element of second type is in corresponding manner affixed to the second and fourth measuring tubes $18_2$, $18_4$, respectively, in the region of 50% of a minimum separation between the first coupling element $24_1$ of first type and the second coupling element $24_2$ of first type, thus at about half the free, oscillatory length of the second and fourth measuring tubes $18_2$, $18_4$, respectively.

In advantageous manner, the coupling elements of second type can supplementally also serve as holders of components of the exciter mechanism 5. Therefore, according to an additional embodiment of the invention, it is provided, that each of the oscillation exciters $5_1$, $5_2$, especially equally constructed oscillation exciters, is held, partially, in each case, on two coupling elements of second type—here, the first and second coupling elements $25_1$, $25_2$—lying opposite to one another. Thus, it can, in very effective and, equally as well, very simple manner, be assured, that the exciter force generated by means of the oscillation exciter $5_1$ effects at least predominantly synchronous, especially also of essentially equal phase to one another, bending oscillations of the first and third measuring tubes $18_1$, $18_3$, or the second and fourth measuring tubes $18_2$, $18_4$. For example, in the case of electrodynamic oscillation exciters, the cylindrical coil can be affixed to the first coupling element of second type and the, in each case, associated permanent magnet to the oppositely lying, second coupling element of second type. For the mentioned case, in which the exciter mechanism 5 has two oscillation exciters $5_1$, $5_2$ both the first oscillation exciter $5_1$ as well as also the second oscillation exciter $5_2$ can, in each case, be held on the first and second coupling elements $25_1$, $25_2$ of second type, for example, also in such a manner, that, as directly evident from FIG. 4, or FIG. 5a, there is a minimum separation between the first and second oscillation exciters $5_1$, $5_2$ of more than twice as large as a tube outer diameter of the measuring tubes $18_1$, $18_2$, $18_3$, $18_4$, at least, however, of the first measuring tube $18_1$. In this way, in total, an optimal exploitation of the available room in the inner space of the transducer housing $7_1$ is enabled, as well as also a simple mounting of the oscillation exciters $5_1$, $5_2$.

According to an additional embodiment of the invention, the measuring transducer comprises, additionally, a third coupling element $25_3$ of second type, for example, again, a plate shaped or rod shaped, coupling element of second type, which is affixed to the first measuring tube $18_1$ and to the third measuring tube $18_3$, but otherwise to no other measuring tube, thus only to the first measuring tube $18_1$ and to the third measuring tube $18_3$, and spaced both from the first coupling element $24_1$ of first type as well as also from the second coupling element $24_2$ of first type, as well as also from the first coupling element $25_1$ of second type, for synchronizing vibrations, especially bending oscillations, of the first measuring tube $18_1$ and thereto equal frequency vibrations, especially bending oscillations, of the third measuring tube $18_3$, as well as a fourth coupling element $25_4$ of second type, especially a plate shaped or rod shaped, coupling element of second type, which is affixed to the second measuring tube $18_2$ and to the fourth measuring tube $18_4$, but otherwise to no other measuring tube, thus only to the second measuring tube $18_2$ and to the fourth measuring tube $18_4$, and spaced both from the first and second coupling elements of first type as well as also from the second and third coupling elements of second type, in each case, for synchronizing vibrations, especially bending oscillations, of the second measuring tube $18_2$ and thereto equal frequency vibrations, especially bending oscillations, of the fourth measuring tube $18_4$. The third and fourth coupling elements $25_3$, $25_4$ of second type are, such as directly evident from the combination of FIGS. 4, 5a and 5b, preferably placed in the measuring transducer 11 lying opposite to one another.

Additionally, the measuring transducer 11 comprises, according to an additional embodiment of the invention, a fifth coupling element $25_5$ of second type, especially a plate shaped or rod shaped fifth coupling element $25_5$ of second type, which is affixed to the first measuring tube $18_1$ and to the third measuring tube $18_3$, but otherwise to no other measuring tube, thus only to the first measuring tube $18_1$ and to the third measuring tube $18_3$, and spaced both from the first and second coupling elements of first type as well as also from the first and third coupling elements of second type, for synchronizing vibrations, especially bending oscillations, of the first measuring tube $18_1$ and of thereto equal frequency vibrations, especially bending oscillations, of the third measuring tube $18_3$, as well as a sixth coupling element $25_6$ of second type, especially a plate shaped or rod shaped, sixth coupling element $25_6$ of second type, which is affixed to the second measuring tube $18_2$ and to the fourth measuring tube $18_4$, but otherwise to no other measuring tube, thus only to the second measuring tube $18_2$ and to the fourth measuring tube $18_4$, and spaced, in each case, both from the first and second coupling elements of first type as well as also from the second, fourth and fifth coupling elements of second type, for synchronizing vibrations, especially bending oscillations, of the second measuring tube and of thereto equal frequency vibrations, especially bending oscillations, of the fourth measuring tube. The fifth and sixth coupling elements $25_5$, $25_6$ of second type are, preferably, again, placed lying opposite to one another in the measuring transducer 11.

Furthermore, it can be of advantage to use the aforementioned coupling elements of second type additionally also for holding individual components of the sensor arrangement. In accordance therewith, it is provided, according to an additional embodiment of the invention, that the inlet-side, first oscillation sensor $19_1$ is held, partially, in each case, on the third and fourth coupling elements $25_3$, $25_4$ of second type. Additionally, the second oscillation sensor $19_2$ is, in corresponding manner, held on the fifth and sixth coupling elements $25_5$, $25_6$ of second type. Thus, it can, in very effective, equally as well very simple manner, be assured, that the oscillation measurement signal generated, during operation, by means of the first oscillation sensor $19_1$ represents. at least predominantly, synchronous, inlet-side, bending oscillations (especially also bending oscillations of equal phase to one another) of the first and third measuring tubes $18_1$, $18_3$ relative to the equally synchronized, inlet-side, bending oscillations (especially also bending oscillations of phase equal to one another) of the second and fourth measuring tubes $18_2$, $18_4$, or that the oscillation measurement signal generated, during operation, by means of the second oscillation sensor $19_2$ represents, at least predominantly, synchronous, outlet-side, bending oscillations (especially also bending oscillations of phase equal to one another) of the first and third measuring tubes $18_1$, $18_3$ relative to the equally synchronized, outlet-side, bending oscillations (especially also bending oscillations of phase equal to one another) of the second and fourth measuring tubes $18_2$, $18_4$. For example, in the case of electrodynamic oscillation sensors, the cylindrical coil of the first oscillation sensor $19_1$ can be affixed to the third coupling element of second type and the associated permanent magnet to the oppositely lying, fourth coupling element of second type, or the cylindrical coil of the second oscillation sensor $19_2$ can be affixed to the fifth, and the associated permanent magnet to the oppositely lying, sixth coupling element of second type. For the mentioned case, in which the sensor arrangement 19 is formed by means of four oscillation sensors $19_1$, $19_2$, $19_3$, $19_4$, according to an additional embodiment of the invention, both the first oscillation sensor $19_1$ as well as also the third oscillation sensor $19_3$ are, in each case, partially held on the third and fourth coupling elements of second type, especially in such a manner, that, such as directly evident from the combination of FIGS. 4, 5a and 5b, a minimum separation between the first and third oscillation sensors $19_1$, $19_3$ is more than twice as large as a tube outer diameter of the first measuring tube $18_1$. In corresponding manner, additionally, also the second oscillation sensor $19_2$ and the fourth oscillation sensor $19_4$ can, in each case, be held on the fifth and sixth coupling elements of second type, especially in such a manner, that, as directly evident from the combination of FIGS. 4, 5a and 5b, a minimum separation between the second and fourth oscillation sensors $19_2$, $19_4$ is more than twice as large as a tube outer diameter of the first measuring tube $18_1$, whereby, in total, an optimal exploitation of the room available in the inner space of the transducer housing $7_1$, as well as also a simple mounting of the oscillation sensors of the sensor arrangement 19, is enabled. Therefore, according to an additional embodiment of the invention, each of the oscillation sensors, especially equally constructed oscillation sensors, of the sensor arrangement 19 is held on two coupling elements of second type lying opposite to one another.

Figure 3A:
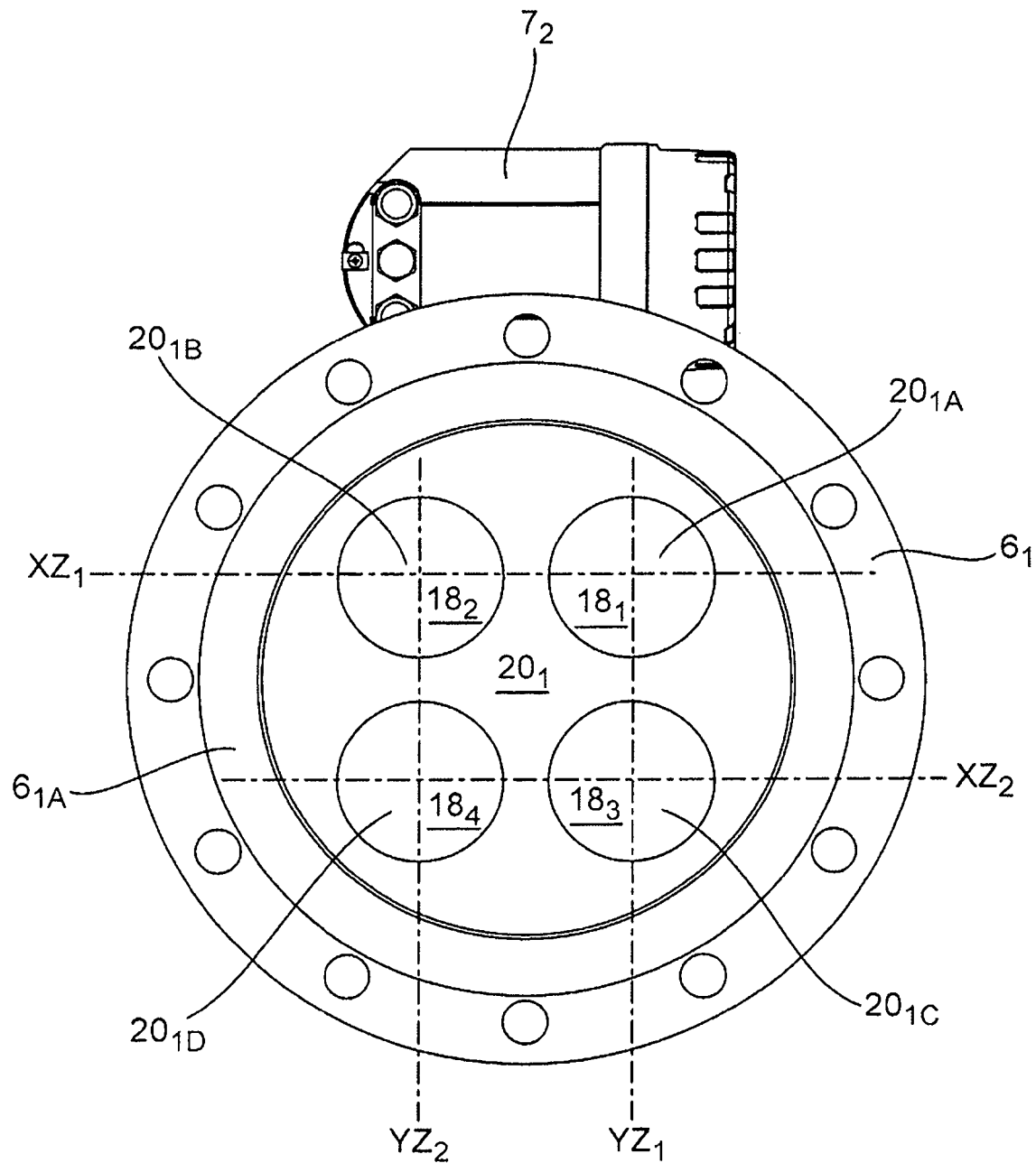
FIGS. 3a, and 3b a projection of the in-line measuring device of FIG. 1 in two different side views.
Figure 3B:
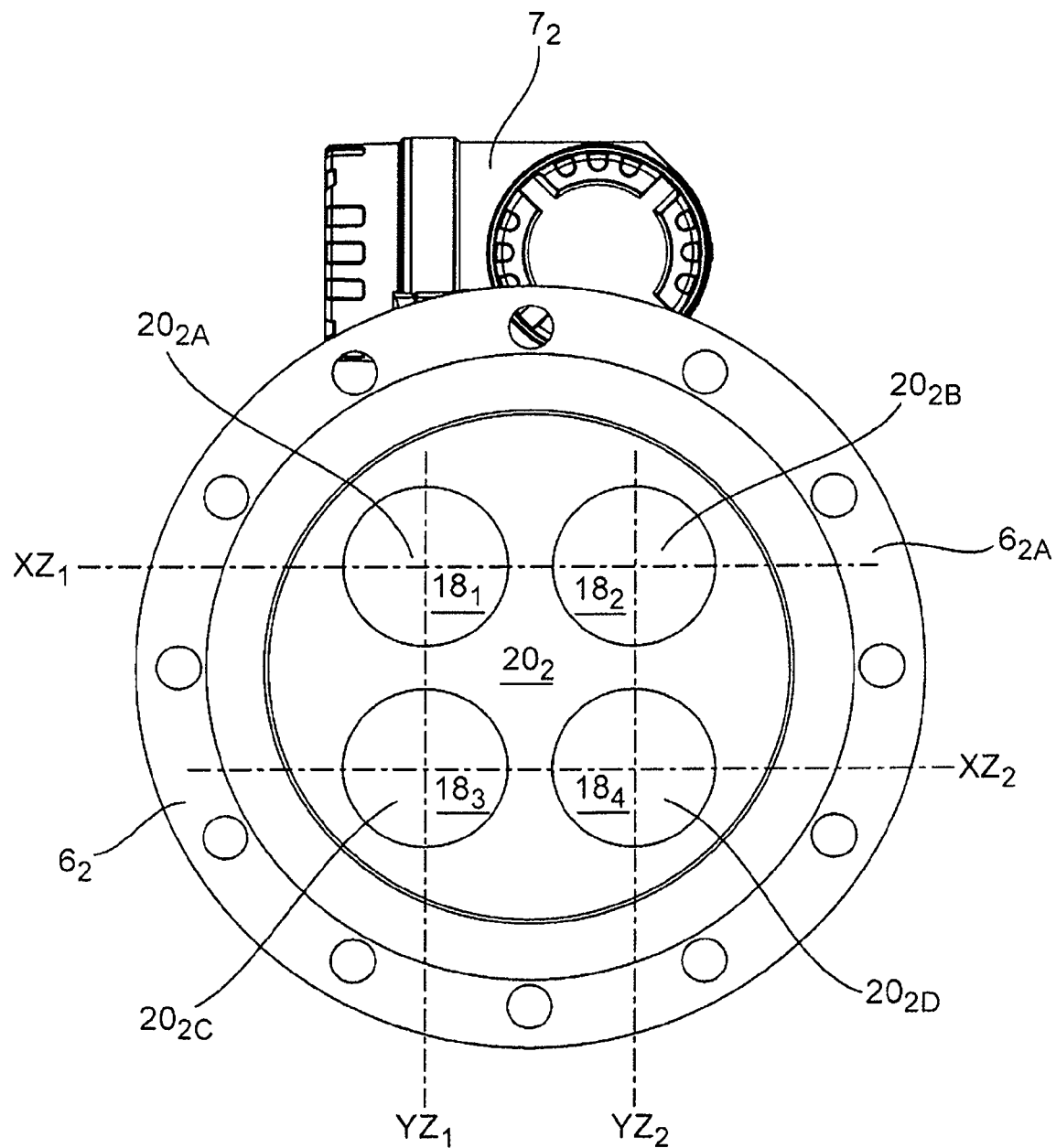

For additional improvement of the oscillation quality factor of the inner part in the case of an as short installed length $L_{11}$ of the measuring transducer 11 as possible, or an as short free, oscillatory length $L_{18x}$ of the measuring tubes $18_1$, $18_2$, $18_3$, or $18_4$ as possible, the measuring transducer comprises, according to an additional embodiment of the invention, a plurality of annular stiffening elements $22_{1A}$, ... $22_{2A}$, ... $22_{3A}$, ... $22_{4A}$, ..., especially annular stiffening elements constructed equally to one another. Each of these stiffening elements is so placed on exactly one of the measuring tubes $18_1$, $18_2$, $18_3$, $18_4$, that it grips around its tube along an imaginary peripheral line thereof, especially a circularly orbiting, peripheral line; compare, in this connection, also the initially mentioned U.S. Pat. No. 6,920,798. Especially, in such case, it is, additionally provided, that at least four of said stiffening elements $22_{1A}$, $22_{1B}$, $22_{1C}$, $22_{1D}$, or $22_{2A}$, $22_{2B}$, $22_{2C}$, $22_{2D}$, or $22_{3A}$, $22_{3B}$, $22_{3C}$, $22_{3D}$, or $22_{4A}$, $22_{4B}$, $22_{4C}$, $22_{4D}$, especially equally constructed stiffening elements, are placed on each of the measuring tubes $18_1$, $18_2$, $18_3$, and $18_4$, respectively. The stiffening elements $22_{1A}$, ... $22_{2A}$, ... $22_{3A}$, ... $22_{4A}$, ... are, in advantageous manner, so placed in the measuring transducer 11, that two adjoining stiffening elements mounted on the same measuring tube have, relative to one another a separation, which amounts to at least 70% of a tube outer diameter of said measuring tube, at most, however, 150% of such tube outer diameter. Found as especially suitable has been, in such case, a separation of neighboring stiffening elements relative to one another, which lies in the range of 80% to 120% of the tube outer diameter of the respective measuring tube $18_1$, $18_2$, $18_3$, and $18_4$, respectively. Alternatively thereto or in supplementation thereof, for improving the oscillation properties of the inner part and, thus, also for improving the measuring accuracy of the measuring transducer, it is additionally provided that the measuring transducer, such as shown schematically in FIGS. 7, 8a, 8b, additionally has plate-shaped stiffening elements $26_1$, $26_2$, $26_3$, $26_4$ for tuning the natural eigenfrequencies of bending oscillations of the measuring tubes $18_1$, $18_2$, $18_3$, and $18_4$, respectively, also in those planes of oscillation $YZ_1$, $YZ_2$, which, as evident in conjunction with the FIGS. 3a, 3b, are essentially perpendicular to the above mentioned planes of oscillation $XZ_1$, $XZ_2$. The, for example, equally constructed, plate-shaped stiffening elements $26_1$, $26_2$, $26_3$, $26_4$ are, in such case, especially so embodied and, in each case, so connected with the measuring tubes, that, as a result, at least the bending oscillation resonance frequencies of the bending oscillations of the measuring tubes $18_1$, $18_2$, $18_3$, and $18_4$, respectively, excited in the wanted mode in the aforementioned—primary—planes of oscillation $XZ_1$, $XZ_2$ are always lower than the natural eigenfrequencies of bending oscillations of the measuring tubes, which are of equal modal order as the wanted mode, but were executed within the—thus, secondary—planes of oscillation $YZ_1$, $YZ_2$. In this way, in very simple, yet very effective manner as regards the respective resonance frequencies of the measuring tubes, a significant separation of the bending oscillation modes of the measuring tubes in the mutually perpendicular—here, primary and secondary—planes of oscillation of the inner part, or of the measuring tubes, can be achieved.

Figure 8A:
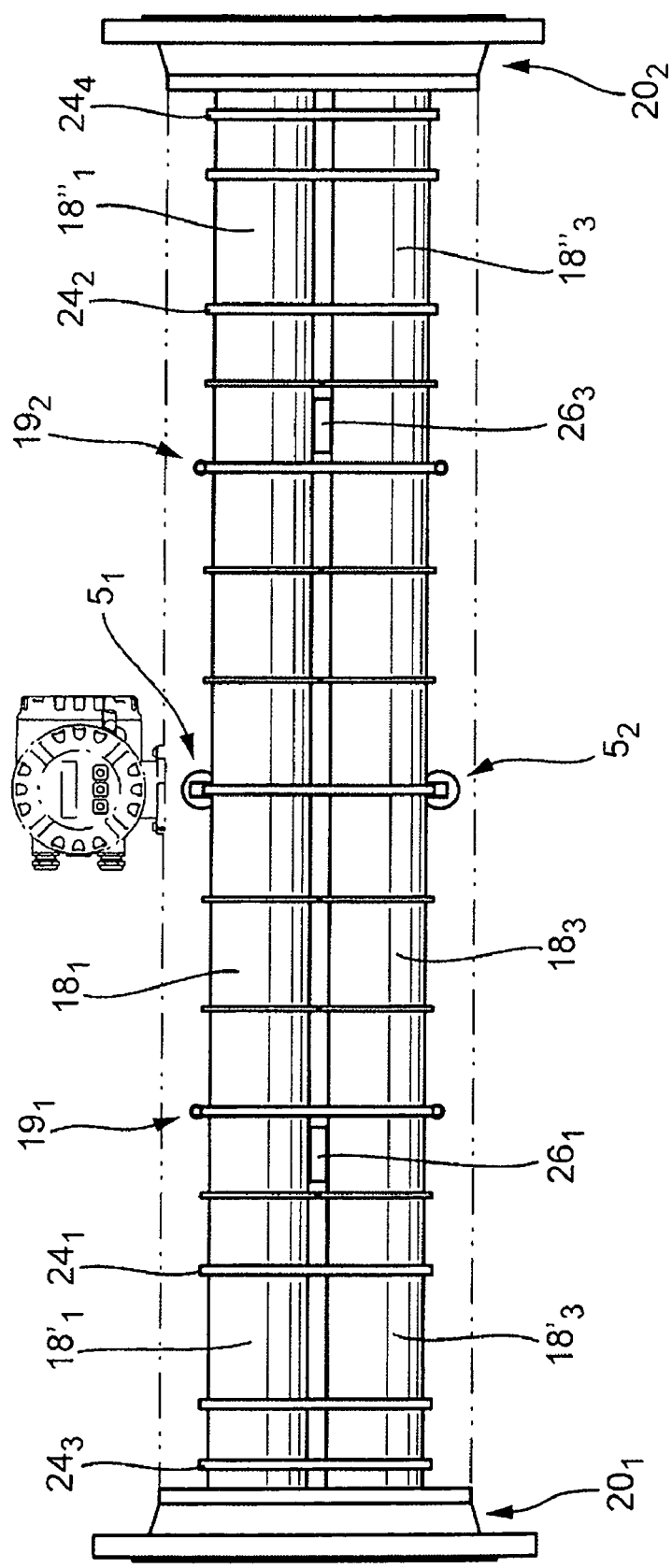
FIGS. 8a, and 8b a projection of the measuring transducer of FIG. 7 in two different side views.
Figure 8B:
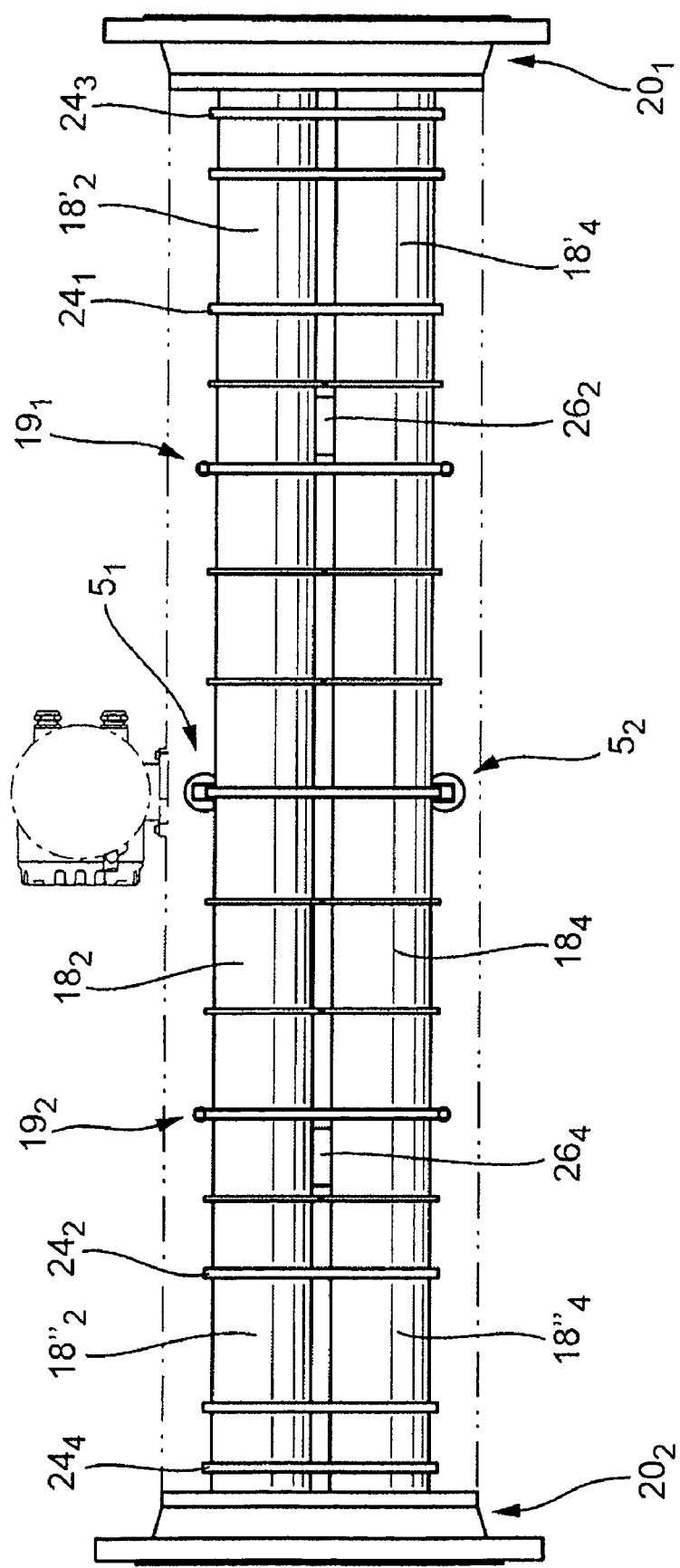

For this purpose, the measuring transducer, in a further embodiment of the invention directly evident from the combination of FIGS. 7, 8a, 8b, has a first plate-shaped stiffening element $26_1$, which, for tuning one or more resonance frequencies of bending oscillations of the first measuring tube $18_1$ and of the third measuring tube $18_3$ in a—secondary—third plane of oscillation $YZ_1$ in each case essentially perpendicular to the—primary—planes of oscillation $XZ_1$, $XZ_2$, is affixed to the first measuring tube $18_1$ and to the third measuring tube $18_3$, and, indeed, in each case, to a segment $18'_1$, $18'_2$ of the first and third measuring tubes $18_1$, $18_3$, respectively, lying between the first oscillation exciter $5_1$ and the first flow divider $20_1$.

Further, the measuring transducer in this embodiment of the invention includes a second plate-shaped stiffening element $26_2$, which, for tuning one or more resonance frequencies of bending oscillations of the second measuring tube $18_2$ and of the fourth measuring tube $18_4$ in a—secondary—fourth plane of oscillation $YZ_2$, in each case, essentially perpendicular to the—primary—planes of oscillation $XZ_1$, $XZ_2$, as well as also essentially parallel to the aforementioned third plane of oscillation $YZ_1$, is affixed to the second measuring tube $18_2$ and to the fourth measuring tube $18_4$, namely, in each case, to a segment $18'_2$, $18'_4$ of the second and fourth measuring tubes $18_2$, $18_4$, respectively, lying between the first oscillation exciter $5_1$ and the first flow divider $20_1$.

Moreover, the measuring transducer includes a third plate-shaped stiffening element $26_3$, which, for tuning said resonance frequencies of bending oscillations of the first measuring tube $18_1$ and of the third measuring tube $18_3$ in the third plane of oscillation $YZ_1$, is affixed to the first measuring tube $18_1$ and to the third measuring tube $18_3$—here, in each case, to a segment $18''_1$, $18''_3$ of the first and third measuring tubes $18_1$, $18_3$, respectively, lying between the first oscillation exciter $5_1$ and the second flow divider $20_2$; as well as a fourth plate-shaped stiffening element $26_4$, which, for tuning said resonance frequencies of bending oscillations of the second measuring tube $18_2$ and of the fourth measuring tube $18_4$ in the fourth plane of oscillation $YZ_2$, is affixed to the second measuring tube $18_2$ and to the fourth measuring tube $18_4$—here, in each case, to a segment $18''_2$, $18''_4$ of the second and fourth measuring tubes $18_1$, $18_4$, respectively lying between the first oscillation exciter $5_1$ and the second flow divider $20_2$. For example, in this case, the first and second plate-shaped stiffening elements $26_1$, $26_2$ can, in each case, be placed between the first oscillation sensor $19_1$ and the first flow divider $20_1$, especially also between the above mentioned first and third coupling elements $24_1$, $24_3$ of first type, while the third and fourth plate-shaped stiffening elements $26_3$, $26_4$ can, in each case, be placed between the second oscillation sensor $19_2$ and the second flow divider $20_2$, especially also between the above mentioned second and fourth coupling elements $24_2$, $24_4$ of first kind. The plate-shaped stiffening elements can, for example, however, also be so arranged in the measuring transducer, that, as also evident from the combination of FIGS. 7, 8a, 8b, the first and second plate-shaped stiffening elements $26_1$, $26_2$ are, in each case, placed between the first coupling element $24_1$ of first type and the first oscillation sensor $19_1$; and the third and fourth plate-shaped stiffening elements $26_3$, $26_4$ are, in each case, placed between the second coupling element $24_2$ of first type and the second oscillation sensor $19_2$.

The plate-shaped stiffening elements can be connected by soldering, brazing or welding with the respective measuring tubes. For example, the stiffening elements can, in such case, be connected with the measuring tubes in a manner such that, as also evident from the combination of FIGS. 7, 8a, 8b, the first plate-shaped stiffening element $26_1$ is affixed to the segment $18'_1$ of the first measuring tube $18_1$ lying between the first oscillation sensor $19_1$ and the first flow divider $20_1$ along one of the straight lateral surface elements of the segment—here, for instance, the one lying nearest to the third measuring tube $18_3$—as well as to the segment $18'_3$ of the third measuring tube $18_3$ lying, as well, between the first oscillation sensor $19_1$ and the first flow divider $20_1$ along a straight lateral surface element thereof—here, for instance, that lying nearest to the first measuring tube. In analogous manner thereto, then also the second plate-shaped stiffening element $26_2$ is affixed to the segments $18'_2$ and $18'_4$, respectively, of the second and fourth measuring tubes $18_2$, $18_4$, lying, in each case, between the first oscillation sensor $19_1$ and the first flow divider $20_1$, the third plate-shaped stiffening element $26_3$ is affixed to the segments $18''_1$ and $18''_3$, respectively, of the first and third measuring tubes $18_1$, $18_3$, lying, in each case, between the second oscillation sensor $19_2$ and the second flow divider $20_2$, and the fourth plate-shaped stiffening element $26_4$ is affixed to the segments $18''_2$ and $18''_4$, respectively, of the second and fourth measuring tubes $18_2$, $18_4$, lying, in each case, between the second oscillation sensor $19_2$ and the second flow divider $20_2$, and, indeed, in each case, along one of the straight lateral surface elements of the respective measuring tube. For achieving a sufficient separation of the resonance frequencies, each of the four plate-shaped stiffening elements $26_1$, $26_2$, $26_3$, $26_4$, according to a further embodiment of the invention, is so embodied and so placed in the measuring transducer that it has a height corresponding to a smallest separation between the lateral surface elements of those two measuring tubes $18_1$, $18_3$ and $18_2$, $18_4$, along which it is, in each case, affixed, which height is smaller than a length of the respective plate-shaped stiffening element $26_1$, $26_2$, $26_3$, $26_4$ measured in the direction of said lateral surface elements, for example in such a manner that the height is less than 50%, especially less than 30%, of said length. Additionally, it is of advantage, when each of the four plate-shaped stiffening elements $26_1$, $26_2$, $26_3$, $26_4$ is additionally, in each case, so embodied that the length of each of the plate-shaped stiffening elements is greater, for example more than two times, especially more than 5 times an associated breadth of the said plate-shaped stiffening element $26_1$, $26_2$, $26_3$, $26_4$ measured transversely to length and height. Alternatively to the affixing to the, in each case, nearest lateral surface elements, the stiffening elements can, however, also, for example, be so embodied and so connected with the measuring tubes, especially also while keeping the aforementioned height to breadth to length relationships, that each of the stiffening elements essentially tangentially contacts the respective two measuring tubes, for example, in each case, along the lateral surface element of each of the measuring tubes lying farthest outwards or farthest inwards.

Through the application of four instead of, such as to this point, two measuring tubes flowed-through in parallel, it is then also possible to manufacture, cost effectively, measuring transducers of the described type also for large mass flow rates, or with large nominal diameters of far over 250 mm, on the one hand, with an accuracy of measurement of over 99.8% at an acceptable pressure drop, especially of about 1 bar or less, and, on the other hand, to keep the installed mass, as well as also the empty mass, of such measuring transducers sufficiently in limits, that, in spite of large nominal diameter, manufacture, transport, installation, as well as also operation can always still occur economically sensibly. Especially also through implementing of above explained measures for further developing the invention—individually or also in combination—, measuring transducers of the type being discussed can also, in the case of large nominal diameter, be so embodied and so dimensioned, that a mass ratio of the measuring transducer, as defined by a ratio of the mentioned empty mass of the measuring transducer to a total mass of the inner part formed by means of the four measuring tubes and the thereto held exciter mechanism, and sensor arrangement, as well as, in given cases, components of the measuring transducer affixed additionally to the measuring tubes and influencing their oscillatory behavior, can be kept directly smaller than 3, especially smaller than 2.5.

The invention claimed is:

1. A measuring transducer of vibration-type for registering at least one physical, measured variable of a flowable medium guided in a pipeline and/or for producing Coriolis forces serving for registering a mass flow rate of a flowable medium, said measuring transducer comprising:

a transducer housing, with an inlet side, first housing end of said transducer housing is formed by means of an inlet-side, first flow divider including four, mutually spaced, flow openings, and with an outlet side, second housing end of said transducer housing is formed by means of an outlet-side, second flow divider including four, mutually spaced, flow openings, said first flow divider including a flange for connecting the measuring transducer to a tubular segment of the pipeline serving for supplying medium to the measuring transducer and said second flow divider including a flange for connecting the measuring transducer to a tubular segment of the pipeline serving for removing medium from the measuring transducer, each of said flanges including respectively, a sealing surface for connecting of the measuring transducer with the corresponding tubular segment of the pipeline;

four, straight, measuring tubes, which are connected to said flow dividers, for guiding flowing medium along flow paths connected in parallel, of which measuring tubes:

a first measuring tube, opens with an inlet-side, first measuring tube end into a first flow opening of said first flow divider and with an outlet-side, second measuring tube end into a first flow opening of said second flow divider, a second measuring tube opens with an inlet-side, first measuring tube end into a second flow opening of said first flow divider and with an outlet-side, second measuring tube end into a second flow opening of said second flow divider, a third measuring tube opens with an inlet-side, first measuring tube end into a third flow opening of said first flow divider and with an outlet-side, second measuring tube end into a third flow opening of said second flow divider, and a fourth measuring tube opens with an inlet-side, first measuring tube end into a fourth flow opening of said first flow divider and with an outlet-side, second measuring tube end into a fourth flow opening of said second flow divider; and an electromechanical exciter mechanism for producing and/or maintaining mechanical oscillations of said four measuring tubes, said exciter mechanism embodied in such a manner, that therewith said first measuring tube and said second measuring tube are excitable, during operation, to execute opposite phase bending oscillations in a shared imaginary first plane of oscillation and said third measuring tube and said fourth measuring tube are excitable, during operation, to execute opposite phase bending oscillations in a shared imaginary, second plane of oscillation, wherein:

a nominal diameter, $D_{11}$, of the measuring transducer, which corresponds to a caliber of the pipeline, in whose course the measuring transducer is to be used, amounts to more than 100 mm, a distance between the sealing surfaces of both flanges defines an installed length, $L_{11}$, of the measuring transducer, said installed length, $L_{11}$, amounts to more than 1200 mm, and each of said four measuring tubes shows a caliber, $D_{18}$, which amounts to more than 60 mm.

2. The measuring transducer as claimed in claim 1, wherein:
said transducer housing is embodied essentially tubularly, especially circularly cylindrically.

3. The measuring transducer as claimed in claim 2, wherein:
said transducer housing has a largest housing inner diameter, $D_7$, which is greater than 150 mm, especially greater than 250 mm.

4. The measuring transducer as claimed in claim 3, wherein:
a housing to measuring tube, inner diameter ratio, $D_7/D_{18}$, the measuring transducer, as defined by a ratio of the largest housing inner diameter, $D_7$, to a caliber, $D_{18}$, of the first measuring tube is greater than 3, especially greater than 4 and/or smaller than 5.

5. The measuring transducer as claimed in claim 4, wherein:
a housing inner diameter to nominal diameter ratio, $D_7/D_{11}$, of the measuring transducer, as defined by a ratio of the largest housing inner diameter, $D_7$, to the nominal diameter, $D_{11}$, of the measuring transducer is smaller than 1.5, especially smaller than 1.2 and/or greater than 0.9, especially in such a manner that the housing inner diameter to nominal diameter ratio, $D_7/D_{11}$, of the measuring transducer is equal to one.

6. The measuring transducer as claimed in claim 1, wherein:
an empty mass, $M_{11}$, of the measuring transducer is greater than 200 kg, especially greater than 300 kg.

7. The measuring transducer as claimed in claim 6, wherein:
a mass to nominal diameter ratio, $M_{11}/D_{11}$, of the measuring transducer, as defined by a ratio of the empty mass, $M_{11}$, of the measuring transducer to the nominal diameter, $D_{11}$, of the measuring transducer, is smaller than 2 kg/mm, especially smaller than 1 kg/mm and/or greater than 0.5 kg/mm.

8. The measuring transducer as claimed in claim 1, wherein:
each of the flanges has a mass of more than 50 kg.

9. The measuring transducer as claimed in claim 1, wherein:
the installed length amounts to less than 3000 mm, and/or the nominal diameter, $D_{11}$, of the measuring transducer amounts to more than 300 mm.

10. The measuring transducer as claimed in claim 9, wherein:
an oscillatory length to installed length ratio, $L_{18x}/L_{11}$, of the measuring transducer, as defined by a ratio of the free, oscillatory length, $L_{18x}$, of said first measuring tube to the installed length, $L_{11}$, of the measuring transducer, amounts to more than 0.55, especially more than 0.6 and/or less than 0.9.

11. The measuring transducer as claimed in claim 9, wherein:
a measuring length to installed length ratio, $L_{19}/L_{11}$, of the measuring transducer, as defined by a ratio of the measuring length, $L_{19}$, to the installed length, $L_{11}$, of the measuring transducer, amounts to more than 0.3, especially more than 0.4 and/or less than 0.7.

12. The measuring transducer as claimed in claim 1, wherein:
a nominal diameter to installed length ratio, $D_1/L_{11}$, of the measuring transducer, as defined by a ratio of the nominal diameter of the measuring transducer to the installed length of the measuring transducer, is smaller than 0.3.

13. The measuring transducer as claimed in claim 12, wherein:
the a nominal diameter to installed length ratio, $D_{11}/L_{11}$, of the measuring transducer is smaller than smaller than 0.2, and/or
the a nominal diameter to installed length ratio, $D_{11}/L_{11}$, of the measuring transducer is greater than 0.1.

14. The measuring transducer as claimed in claim 1, further comprising:
a first coupling element of the first type, especially a plate-shaped, first coupling element, which is affixed on the inlet side at least to said first measuring tube and to said second measuring tube and spaced both from said first flow divider as well as also from said second flow divider, for forming inlet-side, oscillation nodes at least for vibrations, especially bending oscillations, of said first measuring tube and for thereto opposite phase vibrations, especially bending oscillations, of said second measuring tube, especially wherein all four measuring tubes are connected with one another mechanically by means of said first coupling element of the first type, as well as a second coupling element of the first type, especially a plate-shaped, second coupling element and/or a second coupling element constructed equally to said first coupling element and/or a second coupling element parallel to said first coupling element, which is affixed on the outlet side at least to said first measuring tube and to said second measuring tube and spaced both from the first flow divider as well as also from the second flow divider, as well as also from said first coupling element, for forming outlet-side, oscillation nodes at least for vibrations, especially bending oscillations, of said first measuring tube and for thereto opposite phase vibrations, especially bending oscillations, of said second measuring tube, especially wherein all four measuring tubes are connected with one another mechanically by means of said second coupling element of the first type.

15. The measuring transducer as claimed in claim 14, wherein:
said first coupling element of the first type is affixed also to said third measuring tube and to said fourth measuring tube; and
said second coupling element of the first type is affixed to said third measuring tube and to said fourth measuring tube; and/or
a center of mass of said first coupling element of the first type has a distance to a center of mass of the measuring transducer, which is essentially equal to a distance of a center of mass of said second coupling element of the first type to said center of mass of the measuring transducer.

16. The measuring transducer as claimed in claim 14, further comprising:
a third coupling element of the first type, especially a plate-shaped, third coupling element of the first type, which is affixed on the inlet side at least to said third measuring tube and to said fourth measuring tube and spaced both from said first flow divider as well as also from said second flow divider, for forming inlet-side, oscillation nodes at least for vibrations, especially bending oscillations, of said third measuring tube and for thereto opposite phase vibrations, especially bending oscillations, of said fourth measuring tube, especially wherein all four measuring tubes are connected with one another mechanically also by means of said third coupling element of the first type, as well as
a fourth coupling element of the first type, especially a plate-shaped, fourth coupling element of the first type, which is affixed on the outlet side at least to said third measuring tube and to said fourth measuring tube and spaced both from said first flow divider as well as also from said second flow divider, as well as also from said third coupling element of the first type, for forming outlet-side, oscillation nodes at least for vibrations, especially bending oscillations, of said third measuring tube and for thereto opposite phase vibrations, especially bending oscillations, of said fourth measuring tube, especially wherein all four measuring tubes are connected with one another mechanically also by means of said fourth coupling element of the first type.

17. The measuring transducer as claimed in claim 16, wherein:
said third coupling element of the first type is affixed both to said first first measuring tube as well as also to said second measuring tube and spaced, in each case, from said first and said second coupling elements of the first type;
said fourth coupling element of the first type is affixed both to said first measuring tube as well as also to said second measuring tube and spaced, in each case, from said first and said second coupling elements of the first type and/or;
a center of mass of said third coupling element of the first type has a distance to a center of mass of the measuring transducer, which is essentially equal to a distance of a center of mass of said fourth coupling element of the first type to said center of mass of the measuring transducer, especially in such a manner that the distance of the center of mass of said third coupling element of the first type from the center of mass of the measuring transducer is greater than a distance of the center of mass of said first coupling element of the first type from said center of mass of the measuring transducer and greater than a distance of the center of mass of said second coupling element of the first type from said center of mass of the measuring transducer.

18. The measuring transducer as claimed in claim 14, wherein:
a free, oscillatory length, $L_{18x}$, of said first measuring tube, especially of each of said measuring tubes, corresponding to a minimum separation between said first coupling element of the first type and said second coupling element of the first type, amounts to less than 2500 mm, especially less than 2000 mm and/or more than 800 mm.

19. The measuring transducer as claimed in claim 18, wherein:
a caliber to oscillatory length ratio, $D_{18}/L_{18x}$, of the measuring transducer, as defined by a ratio of the caliber, $D_{18}$, of said first measuring tube to the free, oscillatory length, $L_{18x}$, of said first measuring tube, amounts to more than 0.07, especially more than 0.09 and/or less than 0.15.

20. The measuring transducer as claimed in claim 18, wherein:
a measuring length to oscillatory length ratio, $L_{19}/L_{18x}$, of the measuring transducer, as defined by a ratio of the measuring length, $L_{19}$, of the measuring transducer to the free, oscillatory length, $L_{18x}$, of said first measuring tube, amounts to more than 0.6, especially more than 0.65 and/or less than 0.95.

21. The measuring transducer as claimed in claim 14, further comprising:
a first coupling element of the second type, especially a plate shaped or rod shaped, first coupling element of the second type, which is affixed to said first measuring tube and to said third measuring tube, but otherwise to no other measuring tube, and spaced both from said first coupling element of the first type as well as also from said second coupling element of the first type, for synchronizing vibrations, especially bending oscillations, of said first measuring tube and thereto equal frequency vibrations, especially bending oscillations, of said third measuring tube, as well as
a second coupling element of the second type, especially a plate shaped or rod shaped, second coupling element of the second type, which is affixed to said second measuring tube and to said fourth measuring tube, but otherwise to no other measuring tube, and spaced both from said first coupling element of the first type as well as also from said second coupling element of the first type, as well as also from said first coupling element of the second type, for synchronizing vibrations, especially bending oscillations, of the second measuring tube ($18_2$) and thereto equal frequency vibrations, especially bending oscillations, of said fourth measuring tube, especially in such a manner that said first and said second coupling elements of the second type are placed lying opposite one another in the measuring transducer.

22. The measuring transducer as claimed in claim 21, wherein:
said first coupling element of the second type is affixed to said first measuring tube as well as to said third measuring tube in the region of 50% of a minimum separation between said first coupling element of the first type and said second coupling element of the first type; and
said second coupling element of the second type is affixed to said second measuring tube and to said fourth measuring tube in the region of 50% of a minimum separation between said first coupling element of the first type and said second coupling element of the first type.

23. The measuring transducer as claimed in claim 21, further comprising:
a third coupling element of the second type, especially a plate shaped or rod shaped, third coupling element of the second type, which is affixed to said first measuring tube and to said third measuring tube, but otherwise to no other measuring tube, and spaced both from said first coupling element of the first type as well as also from said second coupling element of the first type, as well as also from said first coupling element of the second type, for synchronizing vibrations, especially bending oscillations, of said first measuring tube and thereto equal frequency vibrations, especially bending oscillations, of said third measuring tube, as well as
a fourth coupling element of the second type, especially a plate shaped or rod shaped, fourth coupling element of the second type, which is affixed to said second measuring tube and to said fourth measuring tube, but otherwise to no other measuring tube, and spaced, in each case, both from said first and said second coupling elements of the first type as well as also from said second and said third coupling elements of the second type, for synchronizing vibrations, especially bending oscillations, of said second measuring tube and thereto equal frequency vibrations, especially bending oscillations, of said fourth measuring tube, especially in such a manner that said third and said fourth coupling elements of the second type are placed lying opposite to one another in the measuring transducer.

24. The measuring transducer as claimed in claim 23, further comprising:
a fifth coupling element of the second type, especially a plate shaped or rod shaped, fifth coupling element of the second type, which is affixed to said first measuring tube and to said third measuring tube, but otherwise to no other measuring tube, and spaced both from said first and said second coupling elements of the first type as well as also from said first and said third coupling elements of the second type, for synchronizing vibrations, especially bending oscillations, of said first measuring tube and thereto equal frequency vibrations, especially bending oscillations, of said third measuring tube, as well as
a sixth coupling element of the second type, especially a plate shaped or rod shaped, sixth coupling element of the second type, which is affixed to said second measuring tube and to said fourth measuring tube, but otherwise to no other measuring tube, and spaced, in each case, both from said first and said second coupling elements of the first type as well as also from said second, said fourth and said fifth coupling elements of the second type, for synchronizing vibrations, especially bending oscillations, of said second measuring tube and thereto equal frequency vibrations, especially bending oscillations, of said fourth measuring tube, especially in such a manner that said fifth and said sixth coupling elements of the second type are placed lying opposite to one another in the measuring transducer.

25. The measuring transducer as claimed in claim 1, wherein:
each of said four measuring tubes, especially measuring tubes of equal caliber and/or equal length, has a caliber, $D_{18}$, which amounts to more than 60 mm, especially more than 80 mm.

26. The measuring transducer as claimed in claim 25, wherein:
a caliber to installed length ratio, $D_{18}/L_{11}$, of the measuring transducer, as defined by a ratio of the caliber, $D_{18}$, of said first measuring tube to the installed length, $L_{11}$, of the measuring transducer, amounts to more than 0.02, especially more than 0.05 and/or less than 0.09.

27. The measuring transducer as claimed in claim 25, wherein:
a caliber to measuring length ratio, $D_{18}/L_{19}$, of the measuring transducer, as defined by a ratio of the caliber, $D_{18}$, of the first measuring tube to the measuring length, $L_{19}$, of the measuring transducer, amounts to more than 0.05, especially more than 0.09.

28. The measuring transducer as claimed in claim 1, wherein:
a measuring tube length, $L_{18}$, of said first measuring tube corresponding to a minimum separation between said first flow opening of said first flow divider and said first flow opening of said second flow divider amounts to more than 1000 mm, especially more than 1200 mm and/or less than 2000 mm.

29. The measuring transducer as claimed in claim 28, wherein:
a measuring tube length to installed length ratio, $L_{18}/L_{11}$, of the measuring transducer, as defined by a ratio of the measuring tube length, $L_{18}$, of said first measuring tube to the installed length, $L_{11}$, of the measuring transducer, amounts to more than 0.7.

30. The measuring transducer as claimed in claim 29, wherein:
the measuring tube length to installed length ratio, $L_{18}/L_{11}$, of the measuring transducer amounts to more than 0.8, and/or
the measuring tube length to installed length ratio, $L_{18}/L_{11}$, of the measuring transducer amounts to less than 0.95.

31. The measuring transducer as claimed in claim 1, further comprising:
a sensor arrangement reacting to vibrations (especially bending oscillations excited by means of said exciter mechanism) of said measuring tubes, especially an electrodynamic, sensor arrangement and/or a sensor arrangement formed by means of oscillation sensors constructed equally to one another, for producing oscillation measurement signals representing vibrations, especially bending oscillations, of the measuring tubes.

32. The measuring transducer as claimed in claim 31, wherein:

said sensor arrangement is formed by means of an inlet-side, first oscillation sensor, especially an electrodynamic, first oscillation sensor and/or a first oscillation sensor differentially registering oscillations of said first measuring tube relative to said second measuring tube, as well as by means of an outlet-side, second oscillation sensor, especially an electrodynamic, second oscillation sensor and/or a second oscillation sensor differentially registering oscillations of said first measuring tube relative to said second measuring tube.

33. The measuring transducer as claimed in claim 32, wherein:

said sensor arrangement is formed by means of an inlet-side, third oscillation sensor, especially an electrodynamic, third oscillation sensor, and/or a third oscillation sensor differentially registering oscillations of said third measuring tube relative to said fourth measuring tube, as well as by means of an outlet-side, fourth oscillation sensor, especially an electrodynamic, fourth oscillation sensor and/or a fourth oscillation sensor differentially registering oscillations of said third measuring tube relative to said fourth measuring tube.

34. The measuring transducer as claimed in claim 33, wherein:

said first and said third oscillation sensors are interconnected electrically in series, in such a manner, that a combined oscillation measurement signal represents combined inlet-side oscillations of said first and said third measuring tubes relative to said second and said fourth measuring tube; and said second and said fourth oscillation sensors are interconnected electrically in series, in such a manner, that a combined oscillation measurement signal represents combined outlet-side oscillations of said first and said third measuring tubes relative to said second and said fourth measuring tubes.

35. The measuring transducer as claimed in claim 33, wherein:

said third oscillation sensor is formed by means of a permanent magnet held to said third measuring tube and a cylindrical coil held to said fourth measuring tube and permeated by the magnetic field of the permanent magnet; and said fourth oscillation sensor is formed by means of a permanent magnet held to said third measuring tube and a cylindrical coil held to said fourth measuring tube and permeated by the magnetic field of the permanent magnet.

36. The measuring transducer as claimed in claim 32, wherein:

a measuring length, $L_{19}$, of the measuring transducer corresponding to a minimum separation between said first oscillation sensor and said second oscillation sensor amounts to more than 500 mm, especially more than 600 mm and/or less than 1200 mm.

37. The measuring transducer as claimed in claim 1, wherein:

said four measuring tubes are of equal construction as regards a material, of which their tube walls are composed, and/or as regards their geometric tube dimensions, especially a tube length, a tube wall thickness, a tube outer diameter and/or a caliber.

38. The measuring transducer as claimed in claim 1, wherein:

both said third measuring tube as well as said fourth measuring tube are different from said first measuring tube and said second measuring tube as regards their respective geometric tube dimensions, especially a tube length, a tube wall thickness, a tube outer diameter and/or a caliber.

39. The measuring transducer as claimed in claim 1, wherein:

each of said measuring tubes has a bending oscillation fundamental mode of minimum bending oscillation, resonance frequency; and the minimum bending oscillation, resonance frequencies, at least of said first and said second measuring tubes, are essentially equal and the minimum bending oscillation, resonance frequencies, at least of said third and said fourth measuring tubes.

40. The measuring transducer as claimed in claim 39, wherein:

the minimum bending oscillation, resonance frequencies, of all of said four measuring tubes are essentially equal.

41. The measuring transducer as claimed in claim 39, wherein:

the minimum bending oscillation, resonance frequencies, of said four measuring tubes are only pairwise equal.

42. The measuring transducer as claimed in claim 1, where:

said exciter mechanism is formed by means of a first oscillation exciter, especially an electrodynamic oscillation exciter and/or an oscillation exciter differentially exciting oscillations of said first measuring tube relative to said second measuring tube.

43. The measuring transducer as claimed in claim 42, wherein:

said exciter mechanism is formed by means of a second oscillation exciter, especially an electrodynamic, second oscillation exciter and/or a second oscillation exciter differentially exciting oscillations of said third measuring tube relative to said fourth measuring tube, especially in a manner such that said first and said second oscillation exciters are interconnected electrically in series, in such a manner, that a combined driver signal excites combined oscillations of said first and said third measuring tubes relative to said second and said fourth measuring tubes;

said first oscillation exciter is formed by means of a permanent magnet held to said first measuring tube and a cylindrical coil held to said second measuring tube and permeated by the magnetic field of the permanent magnet; and said second oscillation exciter is formed by means of a permanent magnet held to said third measuring tube and a cylindrical coil held to said fourth measuring tube and permeated by the magnetic field of the permanent magnet.

44. The measuring transducer as claimed in claim 42, wherein:

each of said oscillation exciters, especially equally constructed oscillation exciters, is held, in each case, on two coupling elements of the second type lying opposite to one another.

45. The measuring transducer as claimed in claim 44, wherein:

both said first oscillation exciter as well as also said second oscillation exciter, in each case, are held to said first and said second coupling elements of the second type, especially in such a manner, that a minimum separation between said first and said second oscillation exciters is more than twice as large as a tube outer diameter of said first measuring tube.

46. The measuring transducer as claimed in claim 45, wherein:
both said first oscillation sensor as well as also said third oscillation sensor are held, in each case, to said third and said fourth coupling elements of the second type, especially in such a manner, that a minimum separation between said first and said third oscillation sensors is more than twice as large as a tube outer diameter of said first measuring tube.

47. The measuring transducer as claimed in claim 46, wherein:
both said second oscillation sensor as well as also said fourth oscillation sensor are held, in each case, to said fifth and said sixth coupling elements of the second type, especially in such a manner, that a minimum separation between said second and said fourth oscillation sensors is more than twice as large as a tube outer diameter of said first measuring tube.

48. The measuring transducer as claimed in claim 42, further comprising:
a first plate-shaped stiffening element, which, for tuning resonance frequencies of bending oscillations of said first measuring tube and said third measuring tube in a third plane of oscillation ($YZ_1$) essentially perpendicular to the first and/or second planes of oscillation ($XZ_1$, $XZ_2$), is affixed to said first measuring tube and to said third measuring tube, and, indeed, in each case, to a segment of said first and said third measuring tubes lying between said first oscillation exciter and said first flow divider;
a second plate-shaped stiffening element, which, for tuning resonance frequencies of bending oscillations of said second measuring tube and said fourth measuring tube in a fourth plane of oscillation ($YZ_2$) essentially perpendicular to the first and/or second planes of oscillation ($XZ_1$, $XZ_2$), is affixed to said second measuring tube and to said fourth measuring tube, and, indeed, in each case, to a segment of said second and said fourth measuring tubes lying between said first oscillation exciter and said first flow divider;
a third plate-shaped stiffening element, which, for tuning resonance frequencies of bending oscillations of said first measuring tube and said third measuring tube in the third plane of oscillation ($YZ_1$), is affixed to said first measuring tube and to said third measuring tube, and, indeed, in each case, to a segment of said first and said third measuring tubes lying between said first oscillation exciter and said second flow divider; and
a fourth plate-shaped stiffening element, which, for tuning resonance frequencies of bending oscillations of said second measuring tube and said fourth measuring tube in the fourth plane of oscillation ($YZ_2$), is affixed to said second measuring tube and to said fourth measuring tube, and, indeed, in each case, to a segment of said second and said fourth measuring tubes lying between said first oscillation exciter and said second flow divider.

49. The measuring transducer as claimed in claim 1, wherein:
each of said four measuring tubes, especially measuring tubes of equal caliber, is so arranged, that a smallest lateral separation of each of said four measuring tubes, especially measuring tubes of equal length, from a housing side wall of said transducer housing is, in each case, greater than zero, especially greater than 3 mm and/or greater than twice a respective tube wall thickness;
that a smallest lateral separation between two neighboring measuring tubes is, in each case, greater than 3 mm and/or greater than the sum of their respective tube wall thicknesses, and/or wherein each of said flow openings is so arranged, that a smallest lateral separation of each of said flow openings from a housing side wall of said transducer housing is, in each case, greater than zero, especially greater than 3 mm and/or greater than twice a smallest tube wall thickness of said measuring tubes; and/or that a smallest lateral separation between said flow openings is greater than 3 mm and/or greater than twice a smallest tube wall thickness of said measuring tubes.

50. The measuring transducer as claimed in claim 1, further comprising:
a plurality of annular stiffening element, especially equally constructed stiffening elements, serving for increasing the oscillation quality factor of said measuring tubes, wherein:
each stiffening element is so placed on exactly one of said measuring tubes, that it grips around such along one of its peripheral lines.

51. The measuring transducer as claimed in claim 50, wherein:
on each of said measuring tubes, there are placed at least four of said annular stiffening elements, especially equally constructed stiffening elements;
said stiffening elements are so placed in the measuring transducer, that two adjoining stiffening elements mounted on said same measuring tube have, relative to one another, a separation, which amounts to at least 70% of a tube outer diameter, $D_{18a}$, of said measuring tube ($18_1$; $18_2$; $18_3$; $18_4$), at most, however, 150% of such tube outer diameter, $D_{18}$, especially a separation in the range of 80% to 120% of such tube outer diameter.

52. The measuring transducer as claimed in claim 1, wherein:
a mass ratio, $M_{11}/M_{18}$, of an empty mass, $M_{11}$, of the total measuring transducer to an empty mass, $M_{18}$, of said first measuring tube is greater than 10, especially greater than 15 and smaller than 25, and/or wherein each of said two flow dividers has a mass of more than 20 kg, especially more than 40 kg;
an empty mass, $M_{18}$, of said first measuring tube, especially of each of said measuring tubes, is greater than 20 kg, especially greater than 30 kg and/or smaller than 50 kg;
said first and said second measuring tubes are of equal construction, at least as regards a material, of which their tube walls are, in each case, composed, and/or as regards their geometrical tube dimensions, especially a tube length, a tube wall thickness, a tube outer diameter and/or a caliber;
said third and said fourth measuring tubes are of equal construction, at least as regards a material, of which their tube walls, in each case, are composed, and/or as regards their geometric tube dimensions, especially a tube length, a tube wall thickness, a tube outer diameter and/or a caliber;
both said third measuring tube as well as also said fourth measuring tube differ from said first measuring tube and from said second measuring tube as regards their respective geometric tube dimensions, especially a tube length, a tube wall thickness, a tube outer diameter and/or a caliber;

a material, of which the tube walls of said four measuring tubes are at least partially composed, is titanium and/or zirconium and/or duplex steel and/or super duplex steel;

said transducer housing, said flow dividers and tube walls of said measuring tubes, are composed, in each case, of steel, especially stainless steel;

said four flow openings of said first flow divider are so arranged, that imaginary areal centers of gravity associated with the cross sectional areas, especially circularly shaped, cross sectional areas, of said flow openings of said first flow divider form the vertices of an imaginary square, wherein said cross sectional areas lie in a shared, imaginary, cutting plane of said first flow divider extending perpendicular to a longitudinal axis of the measuring transducer, especially a longitudinal axis parallel to a principal flow axis of the measuring transducer;

said four flow openings of said second flow divider are so arranged, that imaginary areal centers of gravity associated with cross sectional areas, especially circularly shaped, cross sectional areas, of said flow openings of said second flow divider form the vertices of an imaginary square, wherein said cross sectional areas lie in a shared, imaginary, cutting plane of said second flow divider extending perpendicular to a longitudinal axis of the measuring transducer, especially a longitudinal axis parallel to a principal flow axis of the measuring transducer; and/or a middle segment of said transducer housing is formed by means of a straight tube, especially a circularly cylindrical tube.

53. An in-line measuring device for measuring a density and/or a mass flow rate, especially also a total mass flow totaled over a time interval, of a medium, especially a gas, a liquid, a powder or other flowable material, flowing in a pipeline, at least at times, especially with a mass flow rate of more than 2200 t/h, which in-line measuring device, especially an in-line measuring device embodied as a compact device, comprises: a measuring transducer as claimed in claim 1; as well as a measuring device electronics electrically coupled with the measuring transducer, especially also a measuring device electronics mechanically rigidly connected with the measuring transducer.

54. The use of a measuring transducer according to claim 53 for measuring a density and/or a mass flow rate, especially also a total mass flow totaled over a time interval, of a medium, especially a gas, a liquid, a powder or other flowable material, flowing in a pipeline, at least at times, with a mass flow rate of more than 2200 t/h, especially more than 2500 t/h.

* * * * *